United States Patent
Arai et al.

(10) Patent No.: US 9,788,935 B2
(45) Date of Patent: Oct. 17, 2017

(54) COMPOSITE INTERFERENCE SCREWS AND DRIVERS

(71) Applicant: Smith & Nephew, Inc., Memphis, TN (US)

(72) Inventors: Tatsuya Arai, Franklin, MA (US); Mark Edwin Housman, North Attleborough, MA (US); Matthew Edwin Koski, Westford, MA (US)

(73) Assignee: Smith & Nephew, Inc., Memphis, TN (US)

( * ) Notice: Subject to any disclaimer, the term of this patent is extended or adjusted under 35 U.S.C. 154(b) by 204 days.

(21) Appl. No.: 14/805,648

(22) Filed: Jul. 22, 2015

(65) Prior Publication Data
US 2015/0327984 A1  Nov. 19, 2015

Related U.S. Application Data

(63) Continuation of application No. 13/787,139, filed on Mar. 6, 2013, which is a continuation-in-part of
(Continued)

(51) Int. Cl.
*A61F 2/08* (2006.01)
*A61B 17/04* (2006.01)
(Continued)

(52) U.S. Cl.
CPC ........ *A61F 2/0811* (2013.01); *A61B 17/0401* (2013.01); *A61B 17/0466* (2013.01);
(Continued)

(58) Field of Classification Search
CPC ............ A61B 17/0401; A61B 17/0466; A61B 2017/0441; A61B 2017/0445
See application file for complete search history.

(56) References Cited

U.S. PATENT DOCUMENTS 2,288,864 A  7/1942  Whitehead et al.
3,316,795 A  5/1967  Tann
(Continued)

FOREIGN PATENT DOCUMENTS

CN  2732211     10/2005
CN  1701772 A   11/2005
(Continued)

OTHER PUBLICATIONS

Second Office Action for related Chinese Patent Application No. 201280022627.6 issued Sep. 16, 2015.
(Continued)

*Primary Examiner* — Nicholas Woodall
(74) *Attorney, Agent, or Firm* — Burns & Levinson LLP; Joseph M. Maraia

(57) ABSTRACT

The present disclosure relates to an anchor. The anchor includes a suture bridge having a proximal end and distal end. The distal end of the suture bridge has a thickness greater than a thickness of the proximal end of the suture bridge. At least two ribs extend from the proximal end of the suture bridge to a proximal end of the anchor. At least one open helical coil wraps around the at least two ribs and extends, substantially, from the proximal end of the suture bridge to the proximal end of the anchor. The at least one open helical coil defines an internal volume communicating with a region exterior to the anchor through apertures between turns of the at least one open helical coil. The at least two ribs are engagable with a grooved shaft of a driver.

11 Claims, 29 Drawing Sheets

Related U.S. Application Data application No. 13/044,777, filed on Mar. 10, 2011, now Pat. No. 8,979,865.

(60) Provisional application No. 61/334,808, filed on May 14, 2010, provisional application No. 61/359,080, filed on Jun. 28, 2010, provisional application No. 61/312,291, filed on Mar. 10, 2010.

(51) Int. Cl.
*A61B 17/86* (2006.01)
*A61B 17/88* (2006.01)
*A61B 17/00* (2006.01)

(52) U.S. Cl.
CPC .......... *A61B 17/864* (2013.01); *A61B 17/866* (2013.01); *A61B 17/869* (2013.01); *A61B 17/8645* (2013.01); *A61B 17/888* (2013.01); *A61B 17/8877* (2013.01); *A61B 17/8888* (2013.01); *A61F 2/0805* (2013.01); *A61B 2017/00004* (2013.01); *A61B 2017/044* (2013.01); *A61B 2017/0409* (2013.01); *A61B 2017/0441* (2013.01); *A61B 2017/0445* (2013.01); *A61B 2017/0458* (2013.01); *A61B 2017/0464* (2013.01); *A61F 2002/0841* (2013.01); *A61F 2002/0858* (2013.01); *A61F 2002/0888* (2013.01); *A61F 2250/0097* (2013.01)

(56) References Cited

U.S. PATENT DOCUMENTS

| | | |
|---|---|---|
| 3,320,783 A | 5/1967 | Kerr |
| 3,499,222 A | 3/1970 | Linkow et al. |
| 3,716,058 A | 2/1973 | Tanner |
| 3,821,975 A | 7/1974 | Haker |
| 3,869,942 A | 3/1975 | Decaro |
| 3,874,258 A | 4/1975 | Semola et al. |
| 4,027,572 A | 6/1977 | Burge |
| 4,177,797 A | 12/1979 | Baylis et al. |
| D288,777 S | 3/1987 | Kwon |
| 4,653,489 A | 3/1987 | Tronzo |
| 4,738,255 A | 4/1988 | Goble et al. |
| 4,741,651 A | 5/1988 | Despres |
| 4,834,757 A | 5/1989 | Brantigan |
| 4,854,311 A | 8/1989 | Steffee |
| RE33,114 E | 11/1989 | Chiavon |
| 4,913,143 A | 4/1990 | Oloff et al. |
| 4,961,740 A | 10/1990 | Ray et al. |
| 4,988,351 A | 1/1991 | Paulos et al. |
| 5,026,373 A | 6/1991 | Ray et al. |
| 5,055,104 A | 10/1991 | Ray |
| 5,094,133 A | 3/1992 | Schreiber |
| 5,116,337 A | 5/1992 | Johnson |
| 5,129,904 A | 7/1992 | Illi |
| 5,129,906 A | 7/1992 | Ross et al. |
| 5,139,520 A | 8/1992 | Rosenberg |
| 5,197,967 A | 3/1993 | Wilson |
| 5,236,431 A | 8/1993 | Gogolewski et al. |
| 5,242,447 A | 9/1993 | Borzone |
| 5,312,214 A | 5/1994 | Morton |
| 5,354,299 A | 10/1994 | Coleman |
| 5,364,400 A | 11/1994 | Rego, Jr. et al. |
| 5,370,662 A | 12/1994 | Stone et al. |
| 5,383,878 A | 1/1995 | Roger et al. |
| 5,407,427 A | 4/1995 | Zhu et al. |
| 5,411,506 A | 5/1995 | Goble et al. |
| 5,411,523 A | 5/1995 | Goble |
| 5,423,823 A | 6/1995 | Schmieding et al. |
| 5,431,660 A | 7/1995 | Burke |
| 5,447,533 A | 9/1995 | Vachon et al. |
| 5,464,427 A | 11/1995 | Curtis et al. |
| 5,470,334 A | 11/1995 | Ross et al. |
| 5,531,780 A | 7/1996 | Vachon |
| 5,571,139 A | 11/1996 | Jenkins, Jr. |
| 5,573,548 A | 11/1996 | Nazre et al. |
| 5,593,409 A | 1/1997 | Michelson |
| 5,609,635 A | 3/1997 | Michelson |
| 5,609,636 A | 3/1997 | Kohrs et al. |
| 5,626,613 A | 5/1997 | Schmieding |
| 5,632,747 A | 5/1997 | Scarborough et al. |
| 5,645,547 A | 7/1997 | Coleman |
| 5,658,285 A | 8/1997 | Marnay et al. |
| 5,676,545 A | 10/1997 | Jones |
| 5,681,352 A | 10/1997 | Clancy, III et al. |
| 5,688,285 A | 11/1997 | Yamada |
| 5,690,676 A | 11/1997 | Dipoto et al. |
| 5,695,497 A | 12/1997 | Stahelin |
| 5,702,397 A | 12/1997 | Goble et al. |
| 5,709,683 A | 1/1998 | Bagby |
| 5,802,794 A | 9/1998 | Robson |
| 5,833,715 A | 11/1998 | Vachon et al. |
| 5,876,405 A | 3/1999 | Del Rio |
| 5,888,227 A | 3/1999 | Cottle |
| 5,891,146 A | 4/1999 | Simon et al. |
| 5,921,982 A | 7/1999 | Lesh et al. |
| 5,951,560 A | 9/1999 | Simon et al. |
| 5,961,524 A | 10/1999 | Crombie |
| 5,964,783 A | 10/1999 | Grafton et al. |
| 5,968,047 A | 10/1999 | Reed |
| 5,968,098 A | 10/1999 | Winslow |
| 5,984,967 A | 11/1999 | Zdeblick et al. |
| 6,008,433 A | 12/1999 | Stone |
| 6,039,762 A | 3/2000 | McKay |
| 6,086,593 A | 7/2000 | Bonutti |
| 6,096,060 A | 8/2000 | Fitts et al. |
| 6,097,986 A | 8/2000 | Janke et al. |
| 6,132,435 A | 10/2000 | Young |
| 6,146,073 A | 11/2000 | Kobusch |
| 6,196,780 B1 | 3/2001 | Wakai et al. |
| 6,214,031 B1 | 4/2001 | Schmieding et al. |
| 6,235,057 B1 | 5/2001 | Roger et al. |
| 6,283,973 B1 | 9/2001 | Hubbard et al. |
| 6,302,632 B1 | 10/2001 | Lin |
| 6,360,129 B1 | 3/2002 | Ley et al. |
| 6,443,989 B1 | 9/2002 | Jackson |
| 6,447,545 B1 | 9/2002 | Bagby |
| 6,488,683 B2 | 12/2002 | Lieberman |
| 6,503,251 B1 | 1/2003 | Shadduck |
| 6,511,499 B2 | 1/2003 | Schmieding et al. |
| 6,514,257 B2 | 2/2003 | Dovesi et al. |
| 6,517,542 B1 | 2/2003 | Papay et al. |
| 6,527,774 B2 | 3/2003 | Lieberman |
| 6,544,265 B2 | 4/2003 | Lieberman |
| 6,551,319 B2 | 4/2003 | Lieberman |
| 6,551,320 B2 | 4/2003 | Lieberman |
| 6,551,322 B1 | 4/2003 | Lieberman |
| 6,554,830 B1 | 4/2003 | Chappius |
| 6,569,188 B2 | 5/2003 | Grafton et al. |
| 6,589,245 B1 | 7/2003 | Weiler et al. |
| 6,604,945 B1 | 8/2003 | Jones |
| 6,620,195 B2 | 9/2003 | Goble et al. |
| 6,626,917 B1 | 9/2003 | Craig |
| 6,648,903 B1 | 11/2003 | Pierson |
| 6,656,183 B2 | 12/2003 | Colleran et al. |
| 6,666,888 B1 | 12/2003 | Jackson |
| 6,685,728 B2 | 2/2004 | Sinnott et al. |
| 6,818,010 B2 | 11/2004 | Eichhorn et al. |
| 6,823,871 B2 | 11/2004 | Schmieding |
| 6,855,168 B2 | 2/2005 | Crozet |
| 6,857,343 B1 | 2/2005 | Easterbrooks et al. |
| 6,863,671 B1 | 3/2005 | Strobel et al. |
| 6,875,216 B2 | 4/2005 | Wolf |
| 6,887,194 B2 | 5/2005 | Hart et al. |
| 6,908,465 B2 | 6/2005 | von Hoffmann et al. |
| 6,942,669 B2 | 9/2005 | Kurc |
| 6,942,684 B2 | 9/2005 | Bonutti |
| 6,953,462 B2 | 10/2005 | Lieberman |
| 7,018,412 B2 | 3/2006 | Ferreira et al. |
| 7,033,372 B1 | 4/2006 | Cahalan |
| 7,070,586 B2 | 7/2006 | Hart et al. |
| 7,083,647 B1 | 8/2006 | Sklar et al. |

(56) References Cited

U.S. PATENT DOCUMENTS

| | | |
|---|---|---|
| 7,090,690 B2 | 8/2006 | Foerster et al. |
| 7,147,641 B2 | 12/2006 | Chen |
| 7,189,251 B2 | 3/2007 | Kay |
| 7,195,634 B2 | 3/2007 | Schmieding et al. |
| 7,217,279 B2 | 5/2007 | Reese |
| 7,226,469 B2 | 6/2007 | Benavitz et al. |
| 7,235,079 B2 | 6/2007 | Jensen et al. |
| 7,322,978 B2 | 1/2008 | West |
| 7,322,986 B2 | 1/2008 | Wolf |
| 7,335,221 B2 | 2/2008 | Collier et al. |
| 7,371,244 B2 | 5/2008 | Chatlynne et al. |
| 7,442,202 B2 | 10/2008 | Dreyfuss |
| 7,510,558 B2 | 3/2009 | Tallarida et al. |
| 7,572,264 B2 | 8/2009 | Null et al. |
| 7,575,572 B2 | 8/2009 | Sweeney |
| 7,585,311 B2 | 9/2009 | Green et al. |
| 7,594,929 B2 | 9/2009 | Collette |
| 7,601,165 B2 | 10/2009 | Stone |
| 7,601,167 B2 | 10/2009 | Lieberman |
| 7,608,097 B2 | 10/2009 | Kyle |
| 7,608,098 B1 | 10/2009 | Stone et al. |
| 7,749,250 B2 | 7/2010 | Stone et al. |
| 7,857,830 B2 | 12/2010 | Stone et al. |
| 7,867,252 B2 | 1/2011 | Criscuolo et al. |
| 7,883,529 B2 | 2/2011 | Sinnott et al. |
| 7,896,902 B2 | 3/2011 | Jeon et al. |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 7,935,138 B1 | 5/2011 | Richelsoph |
| 7,942,862 B2 | 5/2011 | Hart et al. |
| 7,993,369 B2 | 8/2011 | Dreyfuss et al. |
| 8,034,090 B2 | 10/2011 | Stone et al. |
| 8,118,312 B2 | 2/2012 | Walters |
| 8,167,906 B2 | 5/2012 | Cauldwell et al. |
| 8,251,998 B2 | 8/2012 | Hoeppner et al. |
| 8,252,006 B2 | 8/2012 | Ortiz et al. |
| 8,343,186 B2 | 1/2013 | Dreyfuss et al. |
| 8,372,124 B2 | 2/2013 | Paulk et al. |
| 8,430,909 B2 | 4/2013 | Dreyfuss et al. |
| 8,449,613 B2 | 5/2013 | Crozet |
| 8,480,686 B2 | 7/2013 | Bakos et al. |
| 8,496,662 B2 | 7/2013 | Novak et al. |
| 8,597,328 B2 | 12/2013 | Cauldwell et al. |
| 8,623,049 B2 | 1/2014 | Ward |
| 8,623,052 B2 | 1/2014 | Dreyfuss et al. |
| 8,636,799 B2 | 1/2014 | Sklar et al. |
| 8,663,672 B2 | 3/2014 | Manrique et al. |
| 8,672,967 B2 | 3/2014 | Dimatteo et al. |
| 8,715,282 B2 | 5/2014 | Pool |
| 8,801,755 B2 | 8/2014 | Dreyfuss et al. |
| 8,814,935 B2 | 8/2014 | Paulos |
| 8,821,541 B2 | 9/2014 | Dreyfuss et al. |
| 8,834,538 B2 | 9/2014 | Donnelly et al. |
| 8,900,279 B2 | 12/2014 | Assell et al. |
| 8,974,505 B2 | 3/2015 | Sawa et al. |
| 8,979,848 B2 | 3/2015 | Butters et al. |
| 8,979,865 B2 | 3/2015 | Fan et al. |
| 9,138,220 B2 | 9/2015 | Hernandez |
| 9,155,531 B2 | 10/2015 | Housman |
| 9,162,350 B2 | 10/2015 | Nino et al. |
| 9,237,887 B2 | 1/2016 | Wack et al. |
| 9,265,494 B2 | 2/2016 | Hester et al. |
| 9,277,911 B2 | 3/2016 | Hernandez |
| 9,308,080 B2 | 4/2016 | Housman et al. |
| 9,393,006 B2 | 7/2016 | Housman et al. |
| 9,408,613 B2 | 8/2016 | Kehres et al. |
| 9,427,270 B2 | 8/2016 | Housman |
| 9,439,644 B2 | 9/2016 | Lizardi |
| 9,526,488 B2 | 12/2016 | Arai et al. |
| 9,579,188 B2 | 2/2017 | Bowman et al. |
| 2002/0052629 A1 | 5/2002 | Morgan et al. |
| 2002/0055742 A1 | 5/2002 | Lieberman |
| 2002/0099382 A1 | 7/2002 | Salazar et al. |
| 2002/0111653 A1 | 8/2002 | Foerster |
| 2003/0055431 A1 | 3/2003 | Brannon |
| 2003/0065361 A1 | 4/2003 | Dreyfuss |
| 2003/0065374 A1 | 4/2003 | Honeck |
| 2003/0078585 A1 | 4/2003 | Johnson et al. |
| 2003/0125749 A1 | 7/2003 | Yuan et al. |
| 2003/0195529 A1 | 10/2003 | Takamoto et al. |
| 2004/0030343 A1 | 2/2004 | Kurc |
| 2004/0073216 A1 | 4/2004 | Lieberman |
| 2004/0093032 A1 | 5/2004 | Sinnott et al. |
| 2004/0122424 A1 | 6/2004 | Ferree |
| 2004/0153074 A1 | 8/2004 | Bojarski et al. |
| 2005/0159727 A1 | 7/2005 | Lesh |
| 2005/0222681 A1 | 10/2005 | Richley et al. |
| 2005/0234458 A1 | 10/2005 | Huebner |
| 2005/0250984 A1 | 11/2005 | Lam et al. |
| 2005/0250985 A1 | 11/2005 | Saadat et al. |
| 2005/0250987 A1 | 11/2005 | Ewers et al. |
| 2005/0250988 A1 | 11/2005 | Ewers et al. |
| 2005/0267478 A1 | 12/2005 | Corradi et al. |
| 2006/0030948 A1 | 2/2006 | Manrique et al. |
| 2006/0079895 A1 | 4/2006 | McLeer |
| 2006/0079903 A1 | 4/2006 | Wong |
| 2006/0089651 A1 | 4/2006 | Trudeau et al. |
| 2006/0100627 A1* | 5/2006 | Stone ............... A61B 17/0642 424/426 |
| 2006/0149266 A1 | 7/2006 | Cordasco |
| 2006/0247642 A1 | 11/2006 | Stone et al. |
| 2006/0253080 A1 | 11/2006 | Tulleken et al. |
| 2006/0276841 A1 | 12/2006 | Barbieri et al. |
| 2007/0093895 A1 | 4/2007 | Donnelly et al. |
| 2007/0122764 A1 | 5/2007 | Balfour et al. |
| 2007/0142849 A1 | 6/2007 | Ewers et al. |
| 2007/0198019 A1 | 8/2007 | Schomer et al. |
| 2007/0203498 A1 | 8/2007 | Gerber et al. |
| 2008/0154314 A1 | 6/2008 | McDevitt |
| 2008/0275431 A1 | 11/2008 | Stone et al. |
| 2009/0024174 A1 | 1/2009 | Stark |
| 2009/0042951 A1 | 2/2009 | Danziger |
| 2009/0076544 A1 | 3/2009 | DiMatteo et al. |
| 2009/0118776 A1 | 5/2009 | Kelsch et al. |
| 2009/0125071 A1 | 5/2009 | Skinlo et al. |
| 2009/0187216 A1 | 7/2009 | Schmieding et al. |
| 2009/0292321 A1 | 11/2009 | Collette |
| 2009/0319043 A1 | 12/2009 | McDevitt et al. |
| 2010/0094297 A1 | 4/2010 | Parmigiani |
| 2010/0094352 A1 | 4/2010 | Iott et al. |
| 2010/0106166 A1 | 4/2010 | Cropper et al. |
| 2010/0274298 A1 | 10/2010 | Schiff |
| 2011/0054526 A1 | 3/2011 | Stone et al. |
| 2011/0112576 A1 | 5/2011 | Nguyen et al. |
| 2011/0130760 A1 | 6/2011 | Anderson et al. |
| 2011/0213426 A1 | 9/2011 | Yedlicka et al. |
| 2011/0224727 A1 | 9/2011 | Housman et al. |
| 2011/0319933 A1 | 12/2011 | Tepic |
| 2012/0041448 A1 | 2/2012 | Schumacher et al. |
| 2012/0059384 A1 | 3/2012 | Fan et al. |
| 2012/0179163 A1 | 7/2012 | Housman et al. |
| 2012/0323285 A1* | 12/2012 | Assell ............... A61B 17/8625 606/305 |
| 2012/0330420 A1 | 12/2012 | Brodke et al. |
| 2013/0103080 A1* | 4/2013 | Hernandez ......... A61B 17/0401 606/232 |
| 2013/0158596 A1 | 6/2013 | Miller et al. |
| 2013/0158610 A1 | 6/2013 | Hernandez |
| 2013/0178901 A1 | 7/2013 | Arai et al. |
| 2014/0081339 A1 | 3/2014 | Bowman et al. |
| 2014/0142697 A1 | 5/2014 | Sklar et al. |
| 2014/0148850 A1 | 5/2014 | Dimatteo et al. |
| 2014/0172016 A1 | 6/2014 | Housman |
| 2014/0277129 A1 | 9/2014 | Arai et al. |
| 2014/0277130 A1 | 9/2014 | Housman |
| 2014/0277188 A1 | 9/2014 | Poulos |
| 2014/0277192 A1 | 9/2014 | Housman |
| 2015/0019638 A1 | 1/2015 | Pahlavan et al. |
| 2015/0196388 A1 | 7/2015 | Housman et al. |
| 2015/0327984 A1 | 11/2015 | Arai et al. |
| 2016/0235399 A1 | 8/2016 | Housman et al. |
| 2016/0374661 A1 | 12/2016 | Housman et al. |

(56) References Cited

U.S. PATENT DOCUMENTS

| | | |
|---|---|---|
| 2017/0014224 A1 | 1/2017 | Arai et al. |
| 2017/0020589 A1 | 1/2017 | Bowman et al. |
| 2017/0049438 A1 | 2/2017 | Arai et al. |

FOREIGN PATENT DOCUMENTS

| | | |
|---|---|---|
| CN | 1829479 | 9/2006 |
| CN | 101002703 | 7/2007 |
| CN | 101031248 | 9/2007 |
| CN | 101422381 A | 5/2009 |
| CN | 101573078 | 11/2009 |
| CN | 201436022 U | 4/2010 |
| CN | 102068305 A | 5/2011 |
| CN | 102551821 A | 1/2012 |
| CN | 102475586 | 5/2012 |
| CN | 102512253 A | 6/2012 |
| CN | 102525580 | 7/2012 |
| CN | 102525583 A | 7/2012 |
| CN | 102781370 | 11/2012 |
| CN | 102905636 A | 1/2013 |
| CN | 102573662 B | 8/2015 |
| EP | 0502698 | 9/1992 |
| EP | 05202698 A1 | 9/1992 |
| EP | 0538895 | 6/1993 |
| EP | 0669110 | 11/1995 |
| EP | 0682917 | 11/1995 |
| EP | 0686373 A1 | 12/1995 |
| EP | 0796593 | 3/1998 |
| EP | 0686373 B1 | 3/2001 |
| EP | 1093774 | 4/2001 |
| EP | 1147751 | 10/2001 |
| EP | 1234637 A2 | 8/2002 |
| EP | 1430843 A2 | 6/2004 |
| EP | 1917926 B1 | 11/2009 |
| EP | 2036501 | 9/2010 |
| EP | 2422712 A1 | 2/2012 |
| EP | 2596758 A1 | 5/2013 |
| EP | 2601894 | 6/2013 |
| EP | 2422711 | 10/2015 |
| FR | 2760355 | 9/1998 |
| FR | 2803739 | 7/2001 |
| FR | 2846867 | 5/2004 |
| FR | 2879915 A1 | 6/2006 |
| GB | 2294399 A | 5/1996 |
| JP | H10-000200 | 1/1998 |
| JP | 2005-529650 | 10/2005 |
| JP | 2006212449 A | 8/2006 |
| JP | 2006-305348 A | 11/2006 |
| WO | 1996-08205 | 3/1996 |
| WO | 1996-19947 | 7/1996 |
| WO | 1998-02117 | 1/1998 |
| WO | 1998-26717 | 6/1998 |
| WO | 03063713 A1 | 8/2003 |
| WO | 03103507 A2 | 12/2003 |
| WO | 2006-055516 | 5/2006 |
| WO | 2007093192 A1 | 8/2007 |
| WO | 2008021478 A2 | 2/2008 |
| WO | 2009-042951 | 4/2009 |
| WO | 2010009217 A1 | 1/2010 |
| WO | 2010-017584 | 2/2010 |
| WO | 2010-017631 | 2/2010 |
| WO | 2010053708 A1 | 5/2010 |
| WO | 2011059995 A2 | 5/2011 |
| WO | 2011060022 A2 | 5/2011 |
| WO | 2011-112576 | 9/2011 |
| WO | 2011112776 A1 | 9/2011 |
| WO | 2012-129388 | 9/2012 |
| WO | 2012-171011 | 12/2012 |

OTHER PUBLICATIONS

Substantive Examination for related Mexican Patent Application No. MX/a/2013/010383 issued Aug. 12, 2015.
Patent Examination Report No. 1 for related Australian Patent Application No. 2012229152 Issued Aug. 18, 2015.
Third Office Action for related Chinese Patent Application No. 2011-80013194.3 issued Aug. 21, 2015.
International Preliminary Report on Patentability for related International Application No. PCT/US2014/033535, mailed Oct. 22, 2015.
Decision of Rejection on related Japanese Patent Application No. 2012-557236 mailed Oct. 9, 2015.
Communication from related European Patent Application No. 09761114.9 mailed Dec. 3, 2015.
Communication from related European Patent Application No. 11710940.5 mailed Dec. 8, 2015.
First Office Action for related Chinese Patent Application No. 201280038677.3 issued Sep. 6, 2015.
Patent Examination Report No. 1 for related Australian Patent Application No. 2012267924 mailed Dec. 22, 2015.
Substantive Examination of related Russian Application No. 2013144961/14(069526) mailed Dec. 23, 2015.
Substantive Examination Report from related Mexico Patent Application No. MX/a/2013/010383 mailed Jan. 19, 2016.
Notice of Reasons for Rejection for related Japanese Application No. 2013-558094 mailed Feb. 2, 2016.
Third Office Action from related Chines Application No. 201280022627.6 issued Mar. 4, 2016.
Second Office Action from related Chinese Application No. 201280038677.3 issued May 5, 2016.
International Preliminary Report on Patentability from related PCT Application No. PCT/US2014/066389 issued May 24, 2016.
Office Action from related Mexican Application No. MX/a/2013/010383 issued May 3, 2016.
Notice of Reasons for Rejection from related Japanese Application No. 2014-514625 issued Jun. 13, 2016.
Communication from EPO from related European Application No. 12711719.0-1666 issued Jul. 28, 2016.
Office Action from related Russian Application No. 2015147534/20(073143) issued Jun. 29, 2016.
Office Action from related Japanese Application No. 2013-558094 issued Sep. 5, 2016.
First Office Action from related Chinese Application No. 201480012203.0 issued Aug. 17, 2016.
Office Communication from related European Application No. 14712930.8-1662 issued Nov. 24, 2016.
Office Action and Search Report from related Chinese Application No. 201480032876.2 issued Oct. 19, 2016.
Third Office Action from related Chinese Application No. 201280038677.3 issued Nov. 28, 2016.
Office Action from related Japanese Application No. 2014-514625 issued Dec. 19, 2016.
Office Action from related Russian Application No. 2016124173/20(037886) issued Jan. 19, 2017.
Office Action from related EPO Application No. 14716107.9-1664 issued Mar. 23, 2017.
International Preliminary Report for corresponding PCT Application No. PCT/US020747 mailed Sep. 17, 2015.
Biomet brochure "Bio-Core TM Interference Screw", 2007.
Communication from related European Application No. 14724272.1-1664 issued Jun. 13, 2017.
Decision of Rejections for Japanese Patent Application No. 2011-538642, dated Jun. 2, 2014.
First Office Action for Chinese Patent Application No. 201480073698.8 issued May 2, 2017.
First Office Action for Chinese Patent Application No. 200980155954.7, issued Apr. 2, 2013.
First Office Action for Chinese Patent Application No. 201180013194.3 issued Jul. 21, 2014.
First Office Action for Chinese Patent Application No.: 201280022627.6, issued Apr. 13, 2015.
Hunt, Patrick, D.V.M. et al. "Development of a Perforated Biodegradable Interference Screw", Arthroscopy: Journal of Arthroscopic and Related Surgery, vol. 21, No. 3, Mar. 2005; pp. 258-265.

(56) References Cited

OTHER PUBLICATIONS

International Search and Written Opinion for PCT/US2009/065304 dated Jun. 5, 2013.
International Search and Written Opinion for PCT/US2011/027837 dated May 19, 2011.
International Search and Written Opinion for PCT/US2012/028803 dated Oct. 24, 2010.
International Search and Written Opinion for PCT/US2012/041298 dated Jun. 5, 2013.
International Search and Written Opinion for PCT/US2014/020747 dated Jun. 6, 2014.
International Search and Written Opinion for PCT/US2014/022539 dated Jun. 27, 2014.
International Search and Written Opinion for PCT/US2014/033535 dated Jul. 18, 2014.
International Search and Written Opinion for PCT/US2014/066389 dated Feb. 17, 2015.
Notice of Reasons for Rejection for Japanese Patent Application No. 2012-557236 dated Mar. 2, 2015.
Notice of Reasons for Rejection for Japanese Patent Application No. 2012-557236 dated Nov. 25, 2014.
Notice of Reasons for Rejections for Japanese Patent Application No. 2011-538642, dated Oct. 1, 2013.
Patent Examination Report No. 1 for Australian Patent Application No. 2009319879 issued Nov. 10, 2014.
Patent Examination Report No. 1 for Australian Patent Application No. 2011224326 issued Apr. 21, 2015.
Second Office Action for Chinese Patent Application No. 200980155954.7, issued Oct. 24, 2013.
Second Office Action for Chinese Patent Application No. 201180013194.3, issued Mar. 23, 2015.
Second Office Action from related Chinese Application No. 201480012203.0 issued Apr. 24, 2017.
Smith & Nephew brochure titled "Bio RC™ Bioabsorbable Screws: Anatomically Targeted Screws for ACL and PCL Reconstruction", 2000.
First Office Action from related Chinese Application No. 201480014353.5 issued Apr. 19, 2017.
Second Office Action from related Chinese Application No. 201480032876.2 issued May 31, 2017.
Fourth Office Action from related Chinese Application No. 201280038677.3 issued May 26, 2017.

* cited by examiner

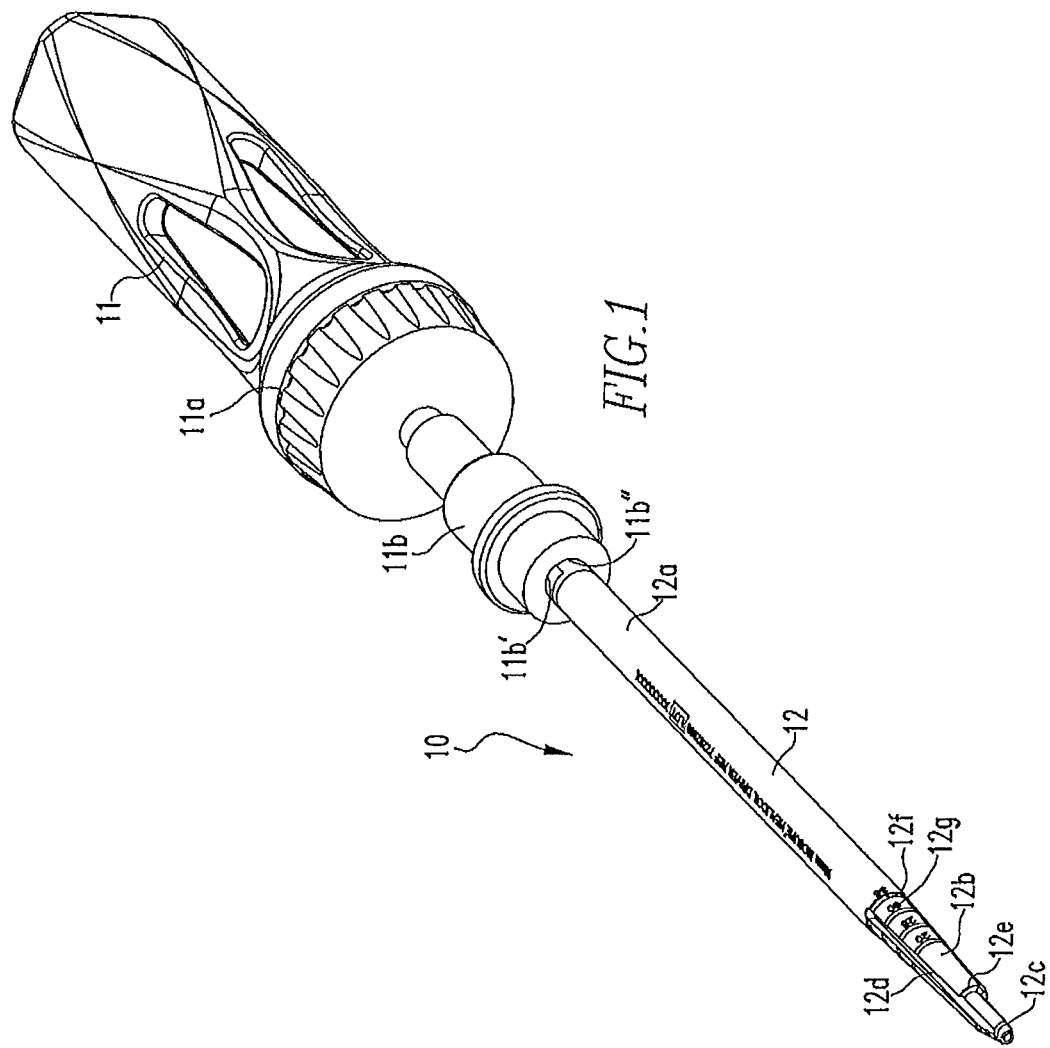

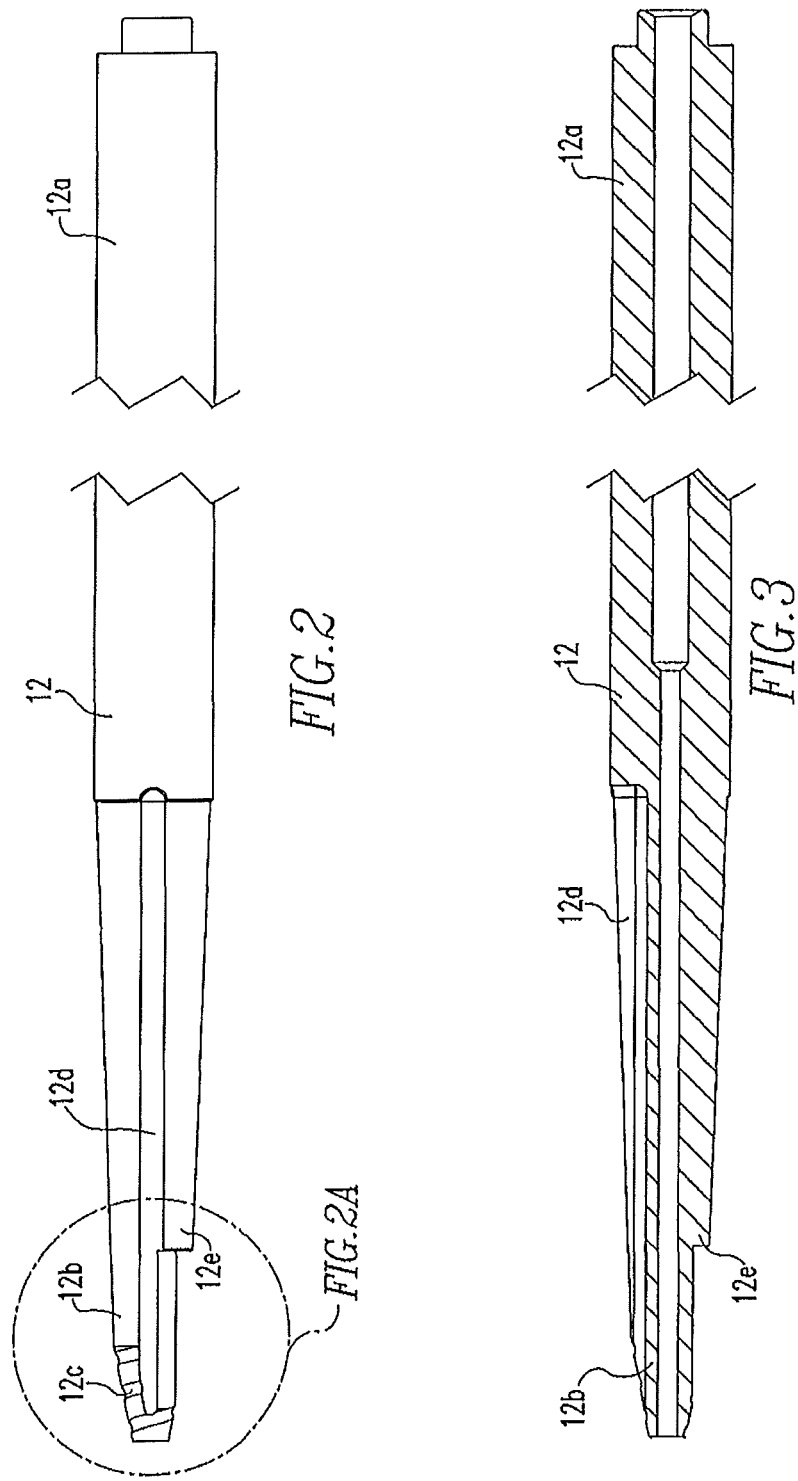

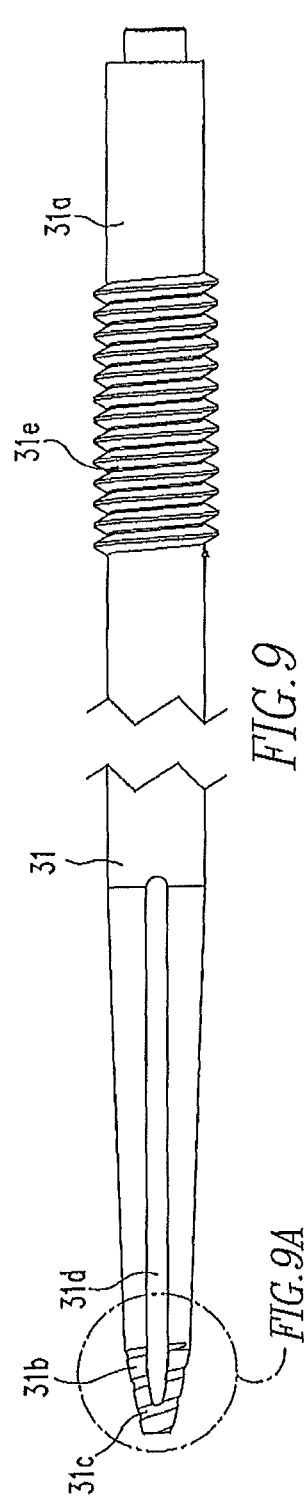
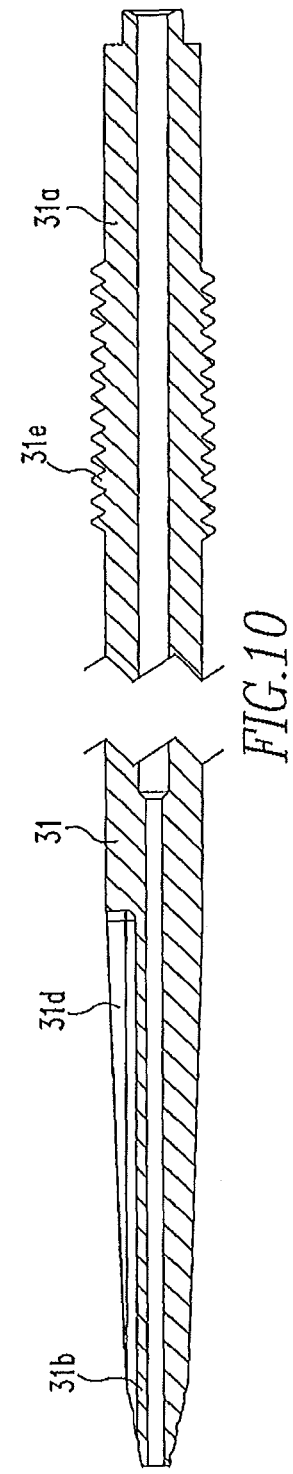

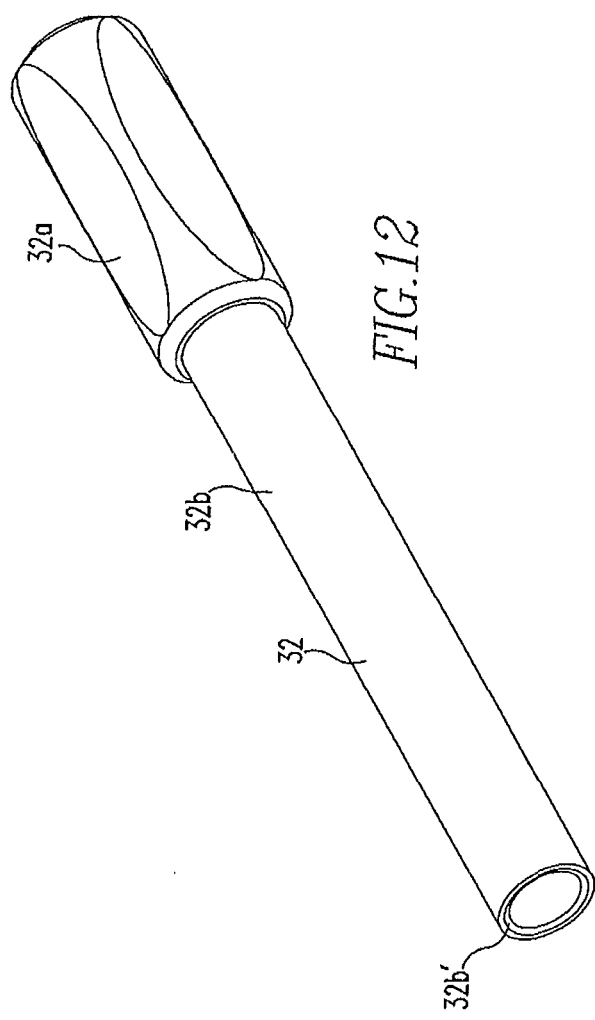
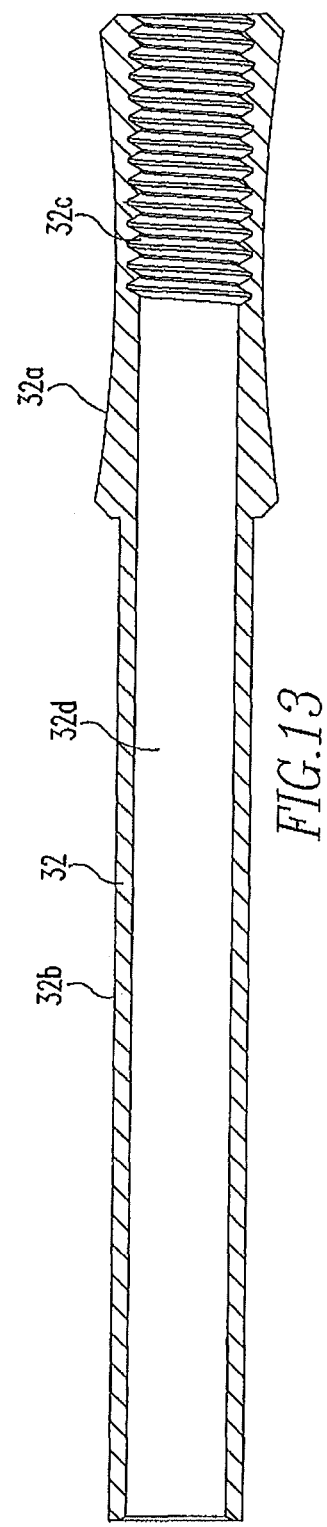
FIG.12
FIG.13

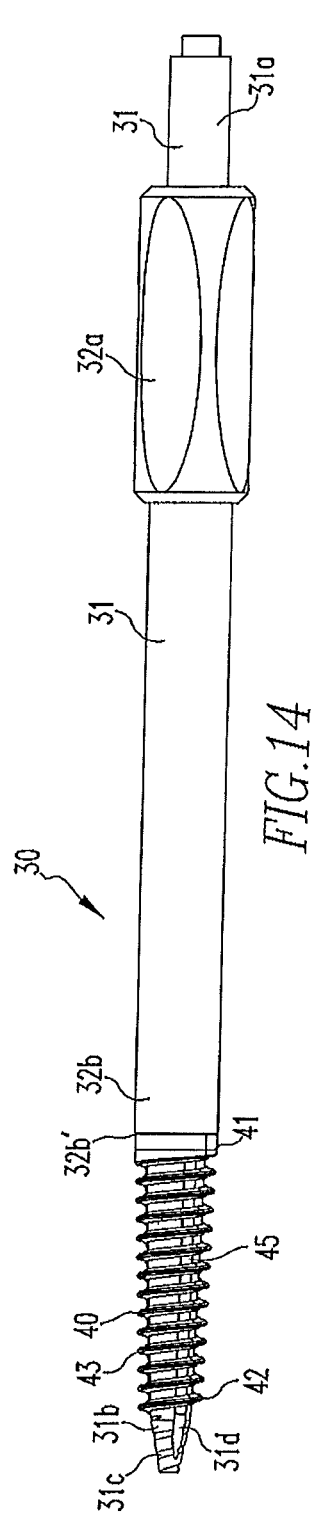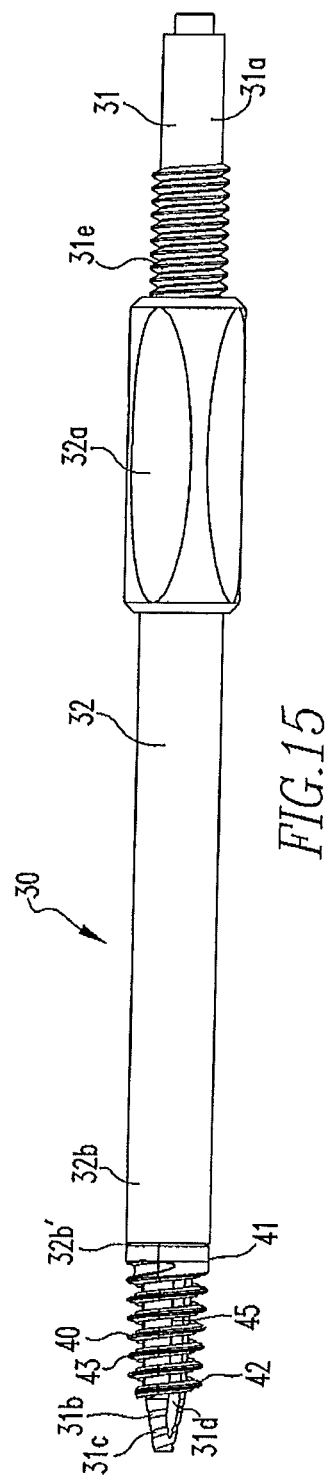

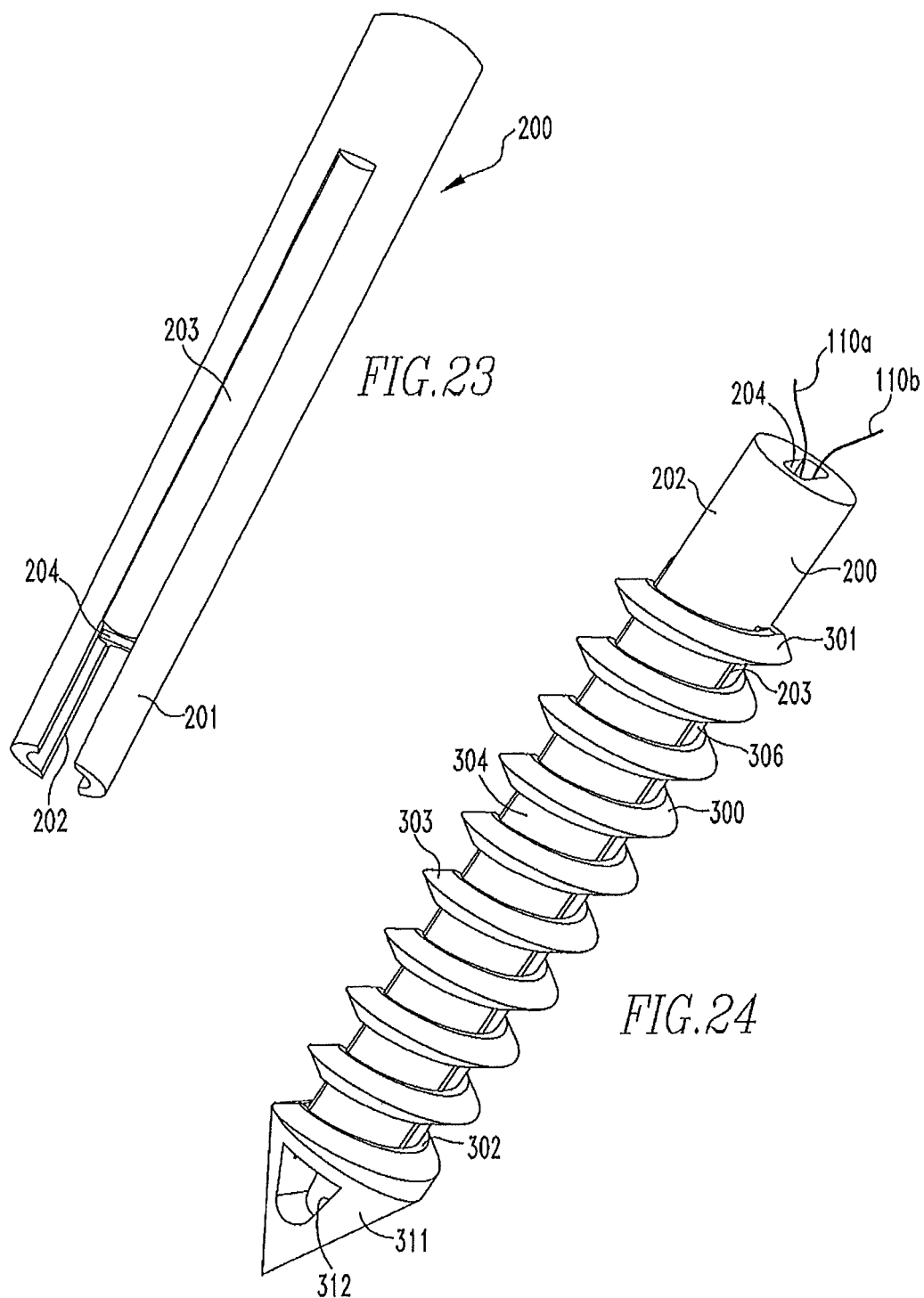

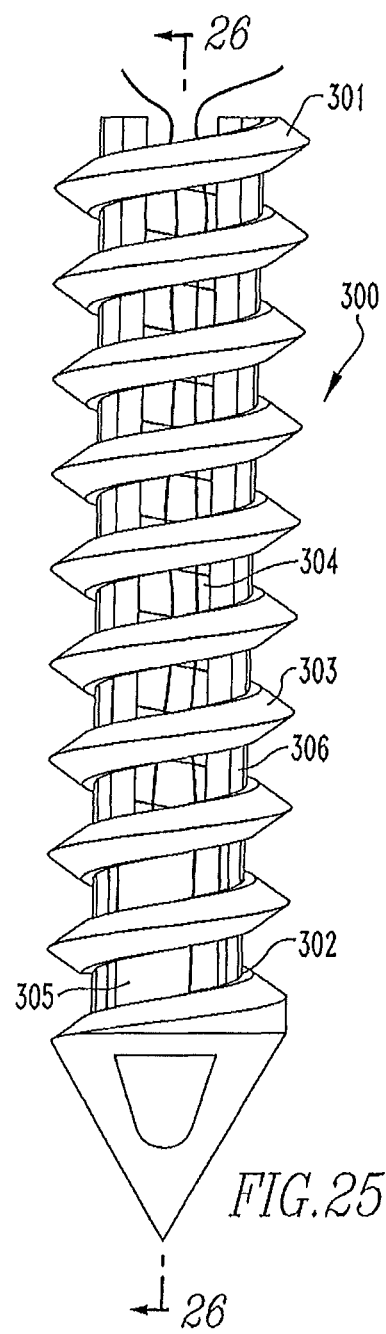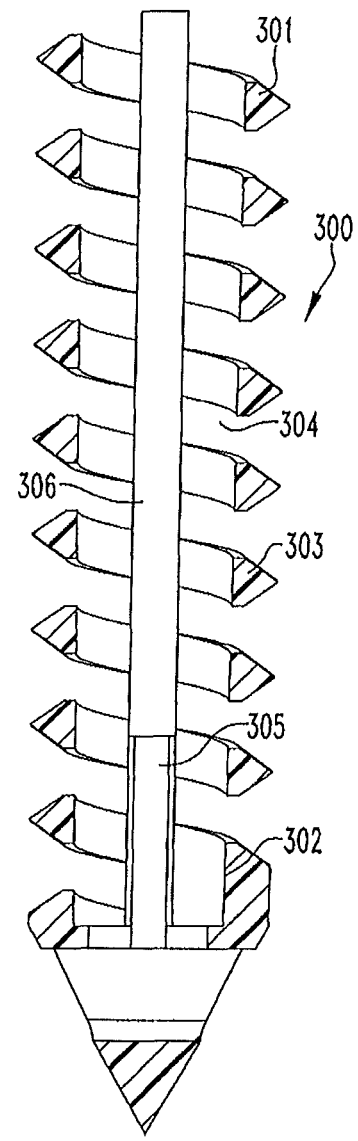
FIG.25
FIG.26

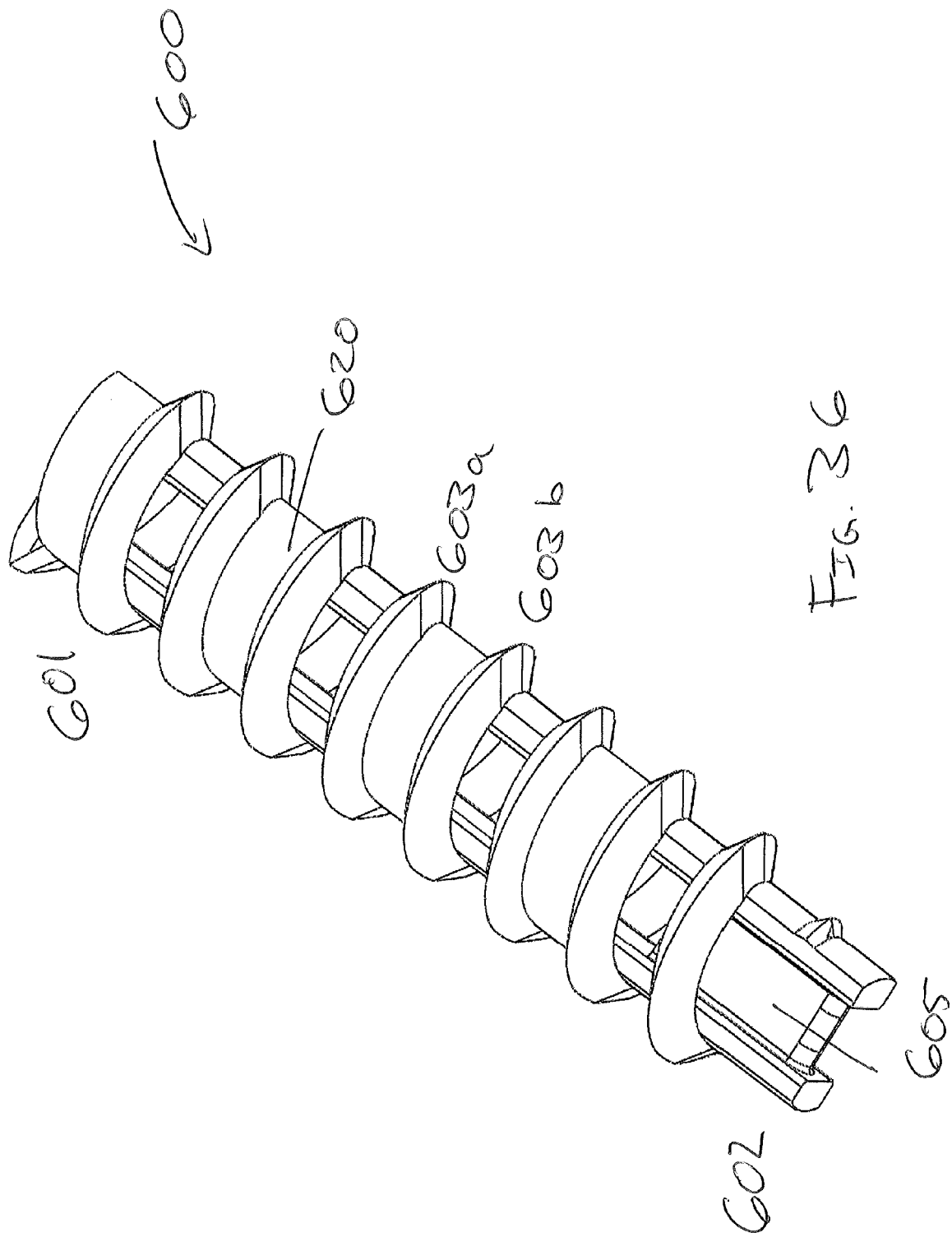

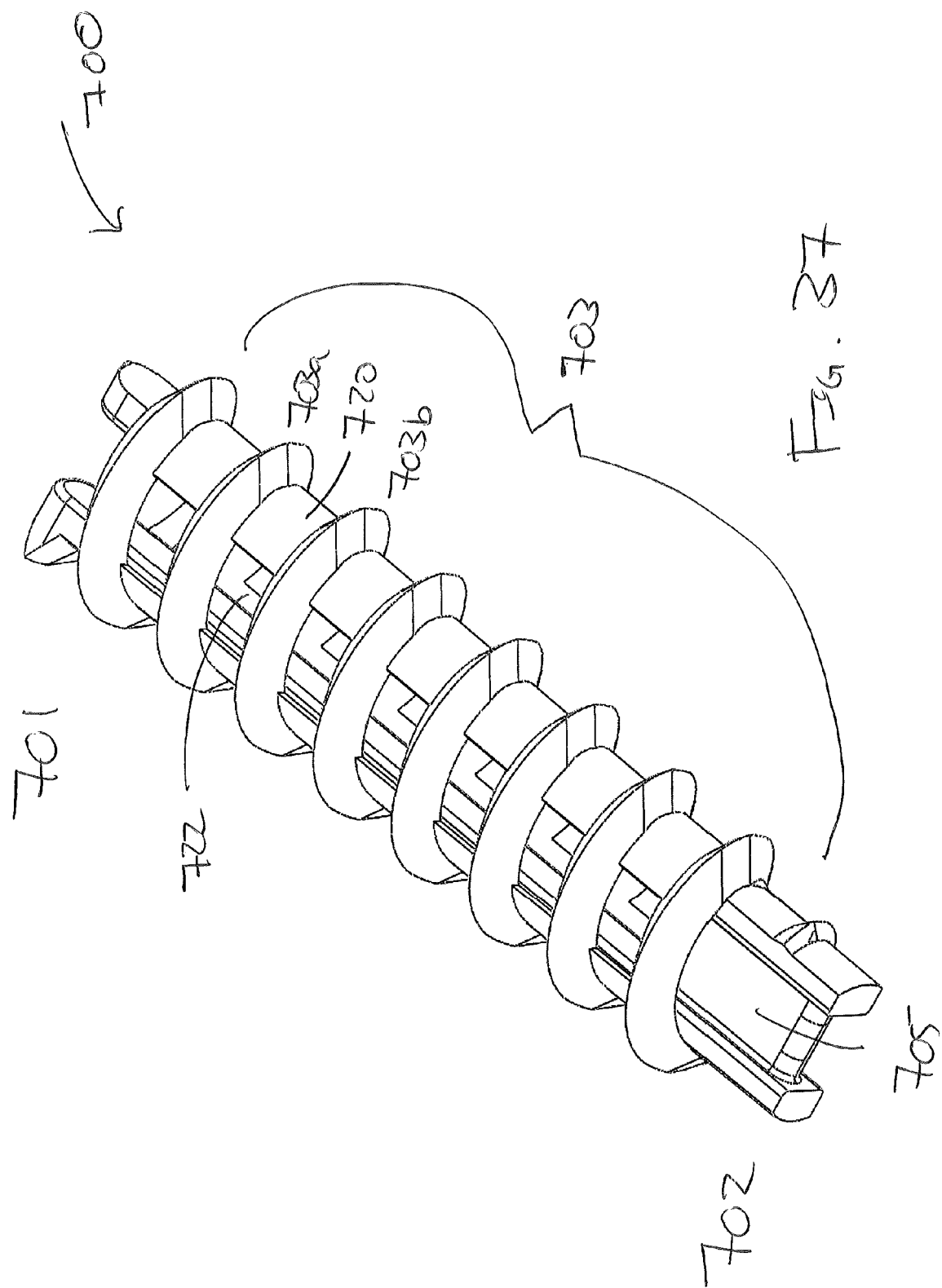

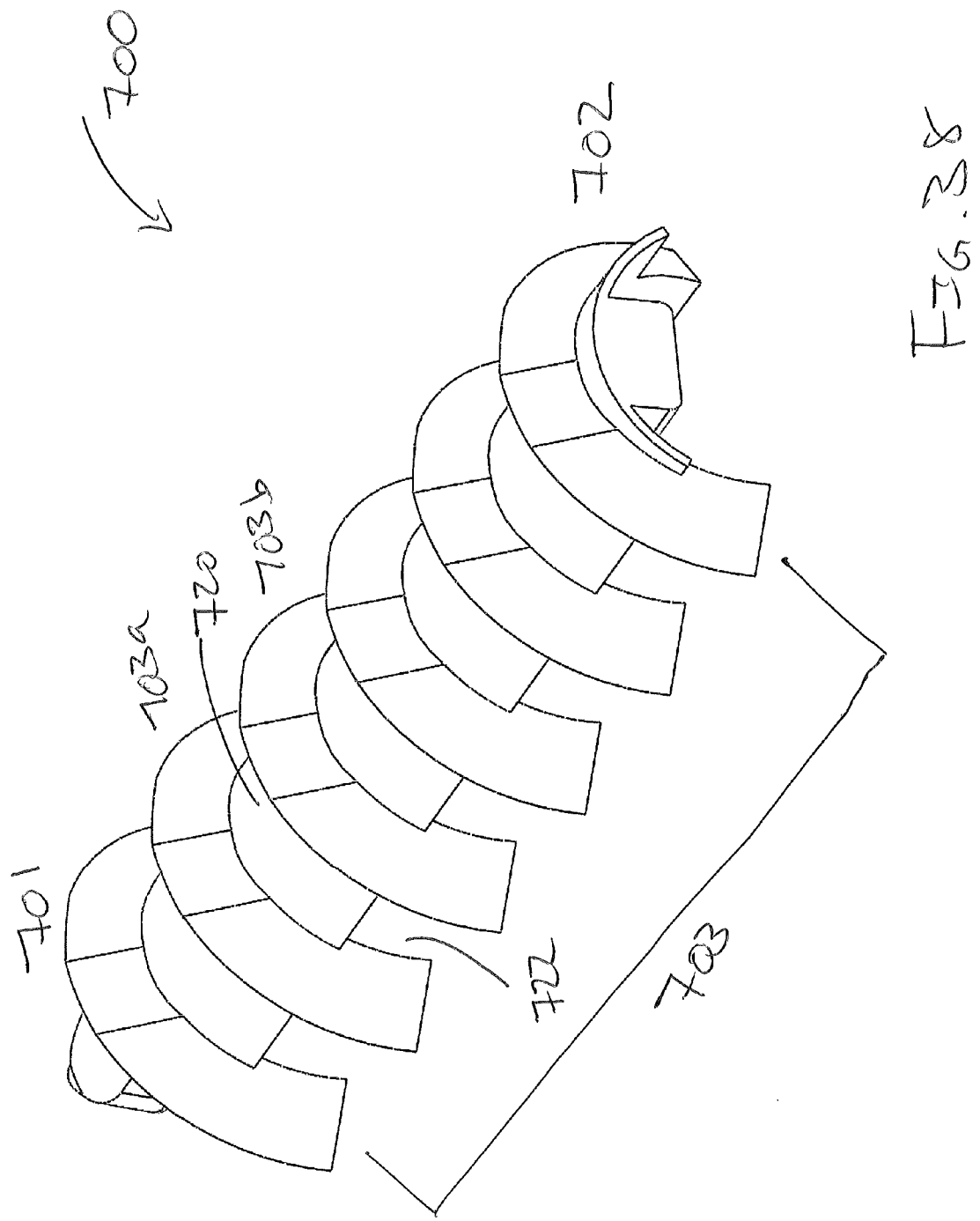

COMPOSITE INTERFERENCE SCREWS AND DRIVERS

CROSS-REFERENCE TO RELATED APPLICATIONS

This application is a continuation of co-pending U.S. application Ser. No. 13/787,139, filed Mar. 6, 2013, entitled COMPOSITE INTERFERENCE SCREWS AND DRIVERS, which in turn is a continuation-in-part application of U.S. application Ser. No. 13/044,777, filed Mar. 10, 2011, which in turn claims priority to U.S. Provisional Application No. 61/312,291, filed Mar. 10, 2010, U.S. Provisional Application No. 61/334,808, filed May 14, 2010, and U.S. Application No. 61/359,080, filed Jun. 28, 2010, the disclosures of which are incorporated herein by reference in their entireties for all purposes.

BACKGROUND

Field of Technology

The present disclosure relates to medical apparatuses and procedures in general, and more particularly to medical apparatuses and procedures for reconstructing a ligament.

Related Art

In many cases, ligaments are torn or ruptured as the result of an accident. Accordingly, various procedures have been developed to repair or replace such damaged ligaments.

For example, in the human knee, the anterior and posterior cruciate ligaments (i.e., the "ACL" and "PCL") extend between the top end of the tibia and the bottom end of the femur. Often, the anterior cruciate ligament (i.e., the ACL) is ruptured or torn as the result of, for example, a sports-related injury. Consequently, various surgical procedures have been developed for reconstructing the ACL so as to restore substantially normal function to the knee.

In many instances, the ACL may be reconstructed by replacing the ruptured ACL with a graft ligament. More particularly, in such a procedure, bone tunnels are generally formed in both the top of the tibia and the bottom of the femur, with one end of the graft ligament being positioned in the femoral tunnel and the other end of the graft ligament being positioned in the tibial tunnel, and with the intermediate portion of the graft ligament spanning the distance between the bottom of the femur and the top of the tibia. The two ends of the graft ligament are anchored in their respective bone tunnels in various ways well known in the art so that the graft ligament extends between the bottom end of the femur and the top end of the tibia in substantially the same way, and with substantially the same function, as the original ACL. This graft ligament then cooperates with the surrounding anatomical structures so as to restore substantially normal function to the knee.

In some circumstances, the graft ligament may be a ligament or tendon which is harvested from elsewhere within the patient's body, e.g., a patella tendon with or without bone blocks attached, a semitendinosus tendon and/or a gracilis tendon.

As noted above, various approaches are well known in the art for anchoring the two ends of the graft ligament in the femoral and tibial bone tunnels.

In one well-known procedure, which may be applied to femoral fixation, tibial fixation, or both, the end of the graft ligament is placed in the bone tunnel, and then the graft ligament is fixed in place using a headless orthopedic screw, generally known in the art as an "interference" screw. More particularly, with this approach, the end of the graft ligament is placed in the bone tunnel and then the interference screw is advanced into the bone tunnel so that the interference screw extends parallel to the bone tunnel and simultaneously engages both the graft ligament and the side wall of the bone tunnel. In this arrangement, the interference screw essentially drives the graft ligament laterally, into engagement with the opposing side wall of the bone tunnel, whereby to secure the graft ligament to the host bone with a so-called "interference fit". Thereafter, over time (e.g., several months), the graft ligament and the host bone grow together at their points of contact so as to provide a strong, natural joinder between the ligament and the bone.

Interference screws have proven to be an effective means for securing a graft ligament in a bone tunnel. However, the interference screw itself generally takes up a substantial amount of space within the bone tunnel, which can limit the surface area contact established between the graft ligament and the side wall of the bone tunnel. This in turn limits the region of bone-to-ligament in-growth, and hence can affect the strength of the joinder. By way of example but not limitation, it has been estimated that the typical interference screw obstructs about 50% of the potential bone-to-ligament integration region.

For this reason, substantial efforts have been made to provide interference screws fabricated from absorbable materials, so that the interference screw can eventually disappear over time and bone-to-ligament in-growth can take place about the entire perimeter of the bone tunnel. To this end, various absorbable interference screws have been developed which are made from biocompatible, bioabsorbable polymers, e.g., polylactic acid (PLA), polyglycolic acid (PGA), etc. These polymers generally provide the substantial mechanical strength needed to advance the interference screw into position, and to thereafter hold the graft ligament in position while bone-to-ligament in-growth occurs, without remaining in position on a permanent basis.

In general, interference screws made from such biocompatible, bioabsorbable polymers have proven clinically successful. However, these absorbable interference screws still suffer from several disadvantages. First, clinical evidence suggests that the quality of the bone-to-ligament in-growth is somewhat different than natural bone-to-ligament in-growth, in the sense that the aforementioned bioabsorbable polymers tend to be replaced by a fibrous mass rather than a well-ordered tissue matrix. Second, clinical evidence suggests that absorption generally takes a substantial period of time, e.g., on the order of three years or so. Thus, during this absorption time, the bone-to-ligament in-growth is still significantly limited by the presence of the interference screw. Third, clinical evidence suggests that, for many patients, absorption is never complete, leaving a substantial foreign mass remaining within the body. This problem is exacerbated somewhat by the fact that absorbable interference screws generally tend to be fairly large in order to provide them with adequate strength, e.g., it is common for an interference screw to have a diameter (i.e., an outer diameter) of 8-12 mm and a length of 20-25 mm.

Thus, there is a need for a new and improved interference fixation system which (i) has the strength needed to hold the graft ligament in position while bone-to-ligament in-growth occurs, and (ii) promotes superior bone-to-ligament in-growth.

SUMMARY

In one aspect, the present disclosure relates to an anchor. The anchor includes a suture bridge having a proximal end and distal end. The distal end of the suture bridge has a thickness greater than a thickness of the proximal end of the suture bridge. At least two ribs extend from the proximal end of the suture bridge to a proximal end of the anchor. At least one open helical coil wraps around the at least two ribs and extends, substantially, from the proximal end of the suture bridge to the proximal end of the anchor. The at least one open helical coil defines an internal volume communicating with a region exterior to the anchor through apertures between turns of the at least one open helical coil. The at least two ribs are engagable with a grooved shaft of a driver.

In yet another aspect, the present disclosure relates to a delivery device and anchor combination. The delivery device of the combination includes a handle and shaft connected to the handle. The shaft includes a distal end having a slot and at least two grooves extending from the slot. The anchor of the combination includes a suture bridge having a proximal end and distal end. The distal end of the suture bridge has a thickness greater than a thickness of the proximal end of the suture bridge. At least two ribs extend from the proximal end of the suture bridge to a proximal end of the anchor. At least one open helical coil wraps around the at least two ribs and extends, substantially, from the proximal end of the suture bridge to the proximal end of the anchor. The at least one open helical coil defines an internal volume communicating with a region exterior to the anchor through apertures between turns of the at least one open helical coil. The anchor is located on the distal end of the delivery device such that the slot houses the proximal portion of the suture bridge and the at least two grooves engage the at least two ribs of the suture bridge.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 1 shows a first embodiment of the delivery device of the present disclosure.

FIG. 2 shows a side view of the shaft of the delivery device of FIG. 1.

FIG. 3 shows a cross-sectional view of the shaft of FIG. 2.

FIG. 9 shows a side view of the inner member of the shaft of FIG. 8.

FIG. 10 shows a cross-sectional view of the inner member of the shaft of FIG. 9.

FIG. 12 shows an isometric view of the outer member of the shaft of FIG. 8.

FIG. 13 shows a cross-sectional view of the outer member of FIG. 12.

FIGS. 14 and 15 show side views of the shaft of FIG. 8 with the outer member in different positions.

FIG. 23 shows an isometric view of the shaft of FIG. 21.

FIG. 24 shows an isometric view of the shaft of FIG. 21 and an alternative screw for use with the shaft.

FIG. 25 shows a side view of the screw of FIG. 24.

FIG. 26 shows a cross-sectional view of the screw of FIG. 24.

FIG. 36 shows an isometric view of another example anchor with suture bridge.

FIG. 37 shows an isometric view of yet another example anchor with suture bridge.

FIG. 38 shows a cross-sectional view of the anchor of FIG. 37.

DETAILED DESCRIPTION OF THE EMBODIMENTS

Figure 2A:
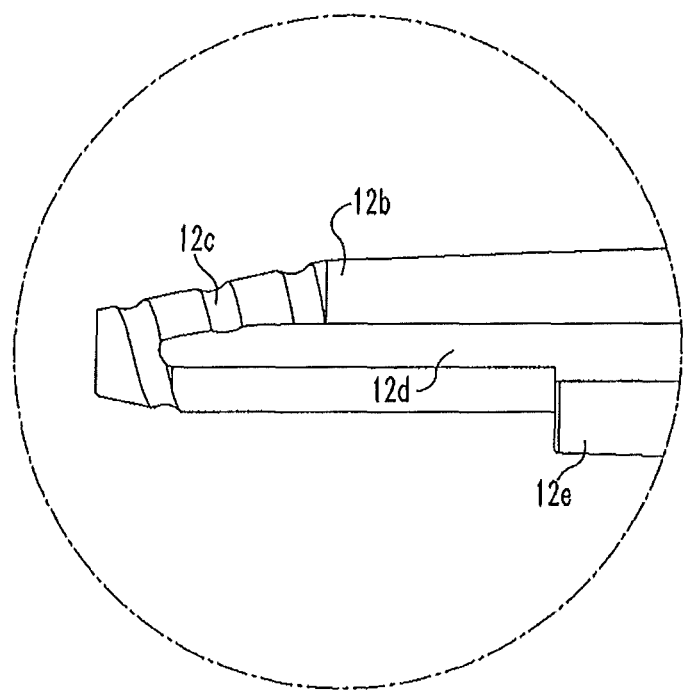
FIG. 2A shows an exploded view of the distal end of the shaft of FIG. 2.
Figure 4:
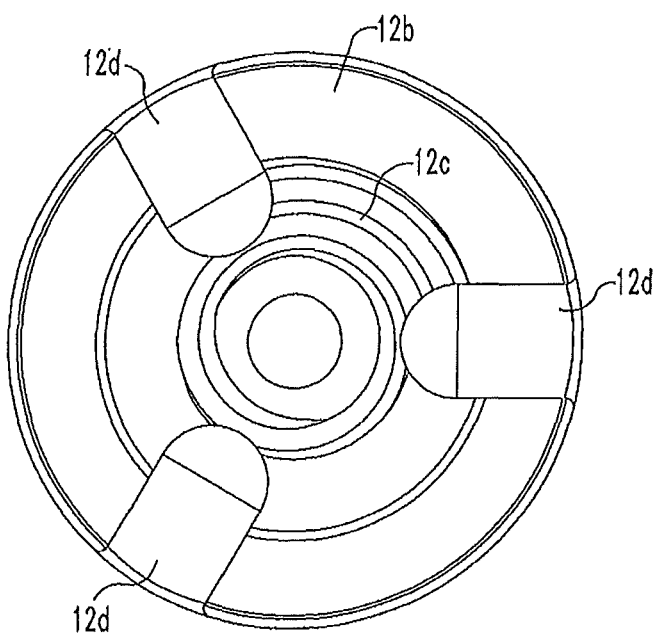
FIG. 4 shows a front view of the distal end of the shaft of FIG. 2.

The following description of the preferred embodiment(s) is merely exemplary in nature and is in no way intended to limit the disclosure, its application, or uses.

FIG. 1 shows a first embodiment of the delivery device 10 of the present disclosure. The device 10 includes a handle assembly 11 and a shaft 12 coupled to the handle assembly 11. The handle assembly 11 includes a handle 11a and a connector 11b coupled to the handle 11a. The connector 11b has a channel 11b' and an opening 11b" to the channel 11b'. The opening 11b" is in the shape of a "D". A proximal end 12a of the shaft 12 is disposed within the channel 11b'.

FIGS. 2, 2A, and 3-4 show the shaft 12. The shaft 12 includes a proximal end 12a and a distal end 12b. The proximal end 12a is in the shape of a "D" to match the shape of the opening 11*b*". The distal end 12*b* includes threads 12*c*, grooves 12*d*, and a depth stop 12*e*. The grooves 12*d* extend a partial length of the shaft 12 and intersect the threads 12*c*. The depth stop 12*e* is for use with a depth stop on a screw that the device 10 is used to implant into a bone tunnel during ligament reconstruction surgery.

Figure 5:
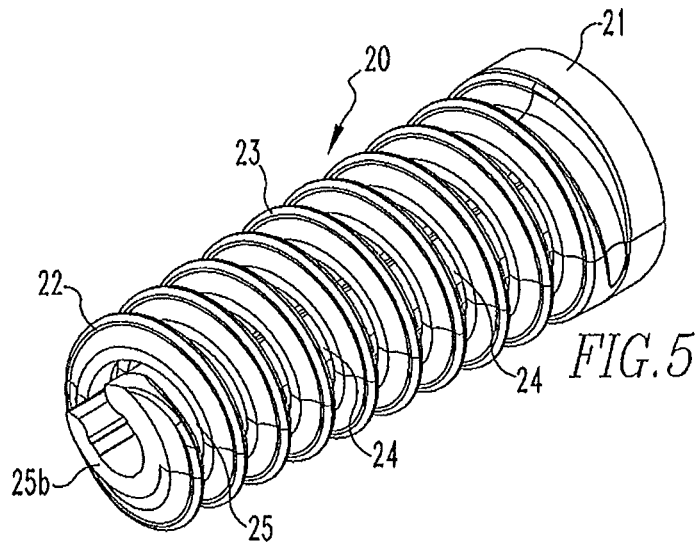
FIG. 5 shows an isometric view of the screw for use with the shaft of FIG. 2.
Figure 6:
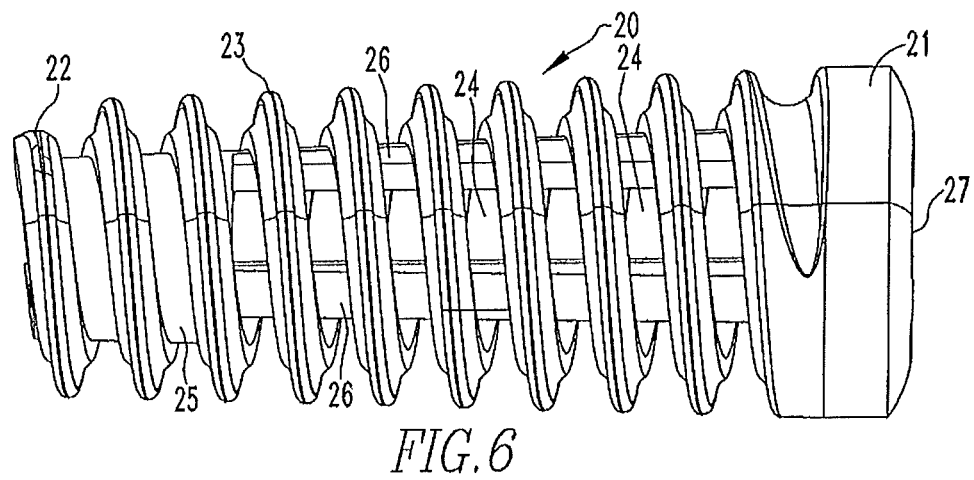
FIG. 6 shows a side view of the screw of FIG. 5.
Figure 7:
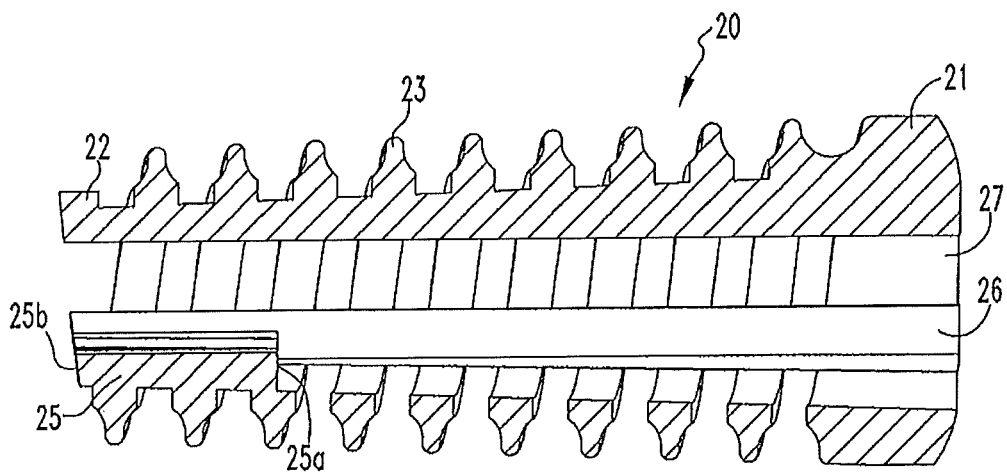
FIG. 7 shows a cross-sectional view of the screw of FIG. 6.
Figure 8:
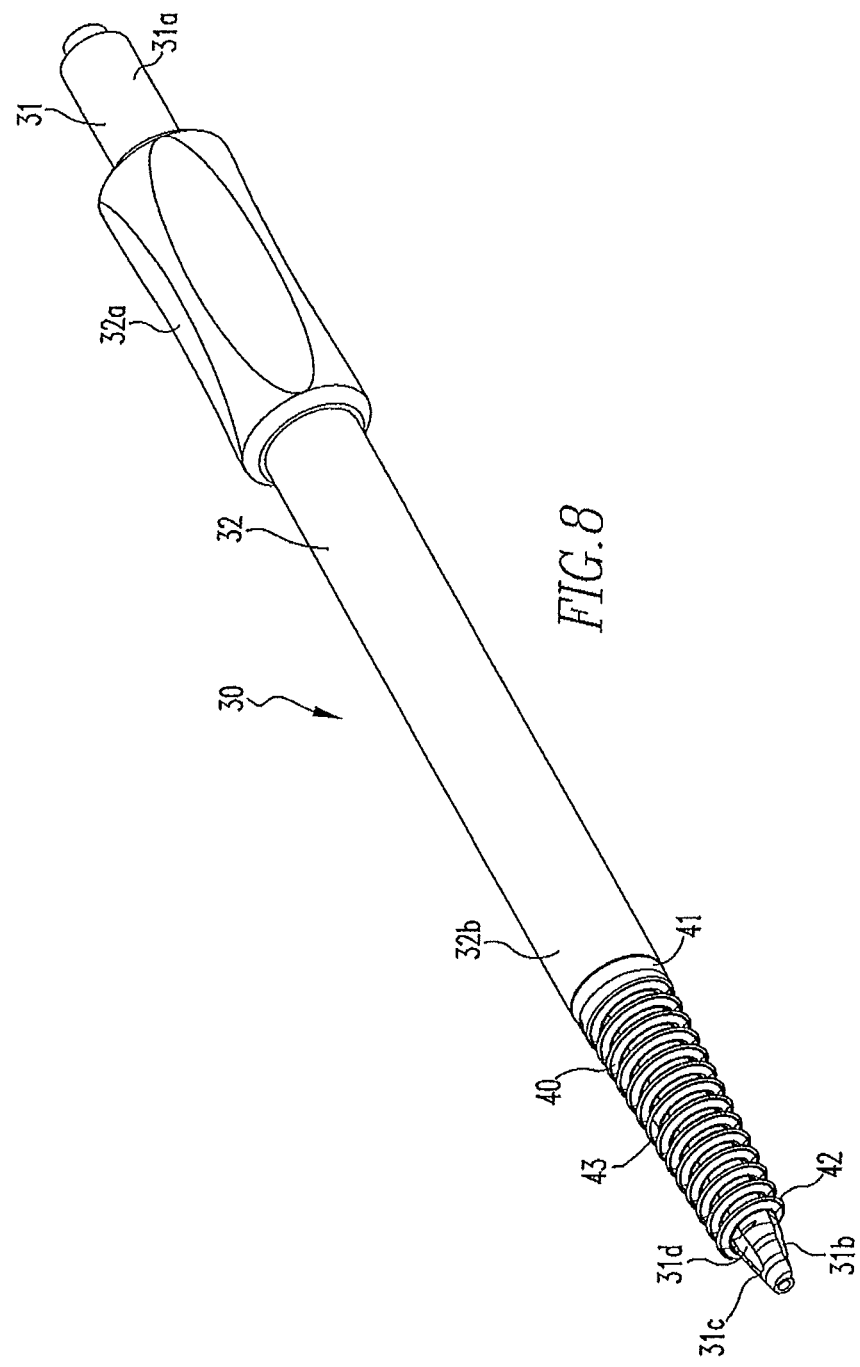
FIG. 8 shows a second embodiment of a shaft of the present disclosure.
Figure 9A:
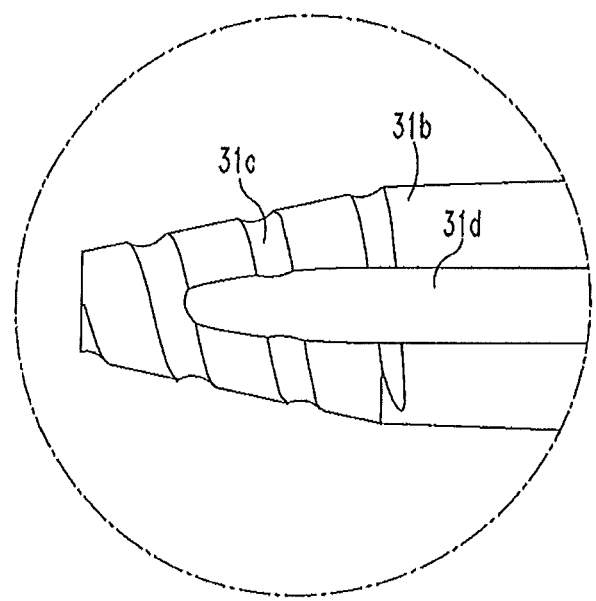
FIG. 9A shows an exploded view of the distal end of the inner member of FIG. 9.
Figure 11:
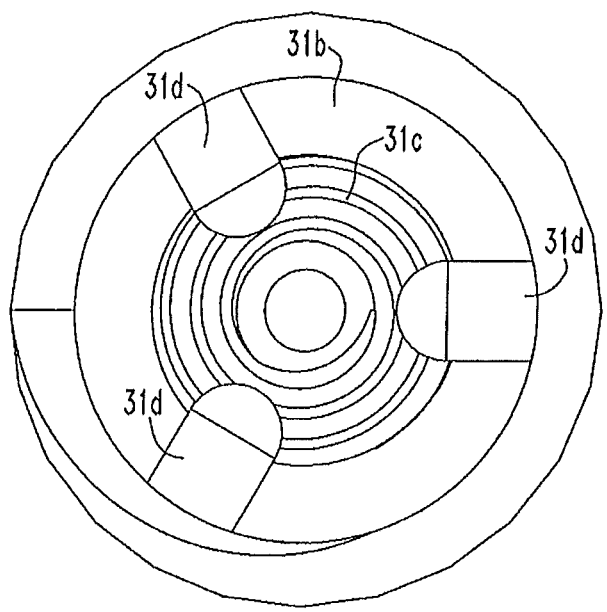
FIG. 11 shows a front view of the distal end of the inner member of FIG. 9.
Figure 16:
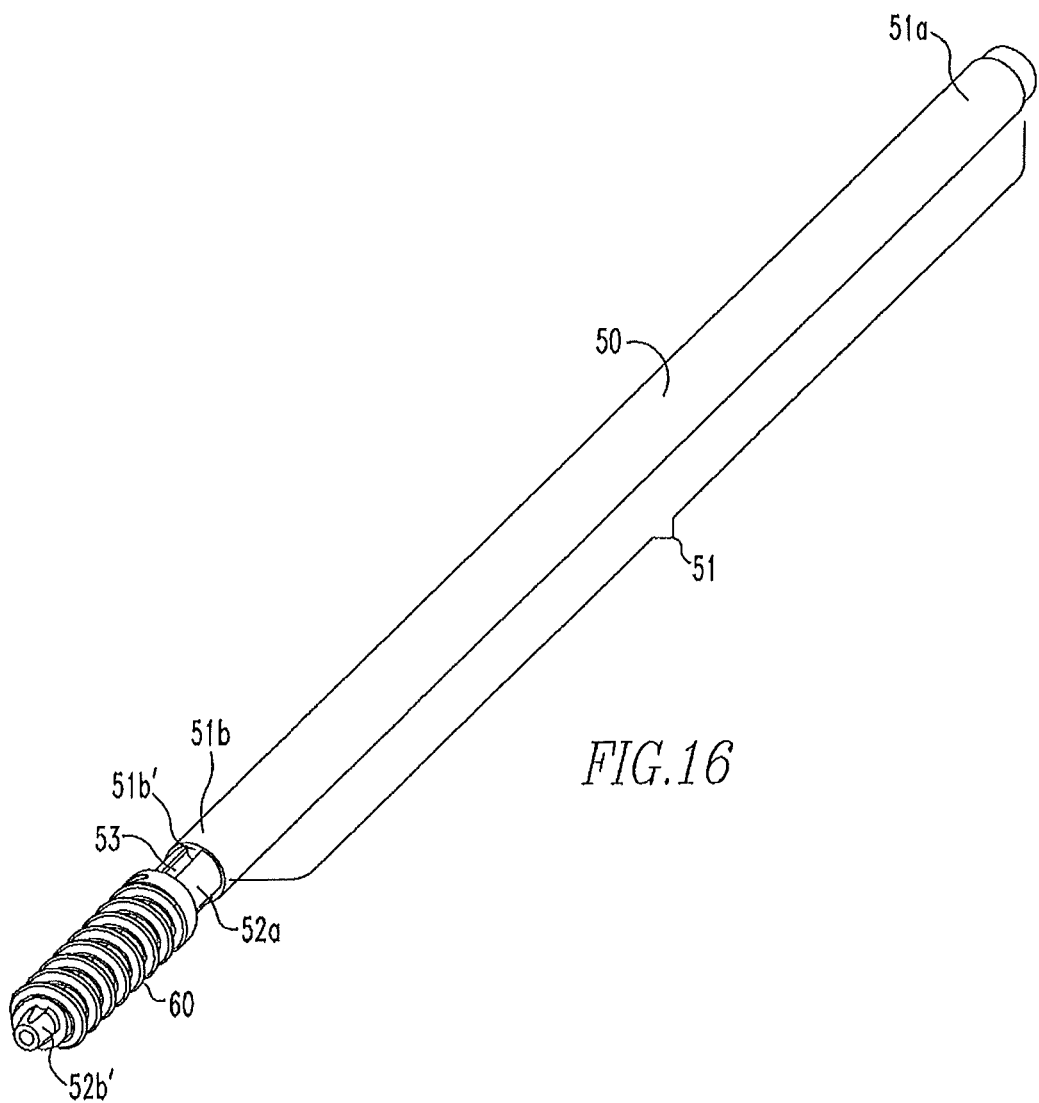
FIG. 16 shows an isometric view of a third embodiment of a shaft of the present disclosure and a screw for use with the shaft.
Figure 17:
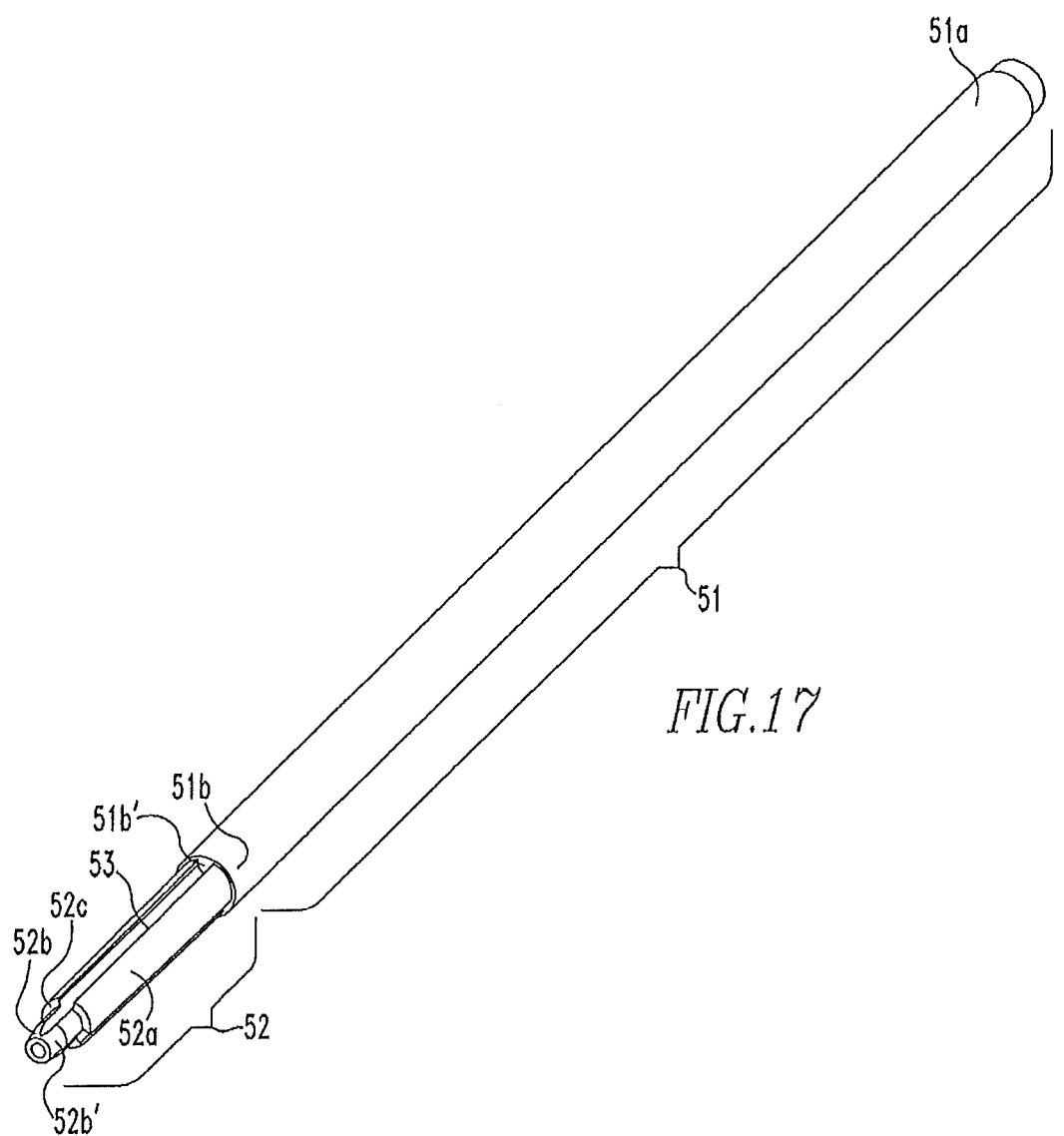
FIG. 17 shows an isometric view of the shaft of FIG. 16.
Figure 18:
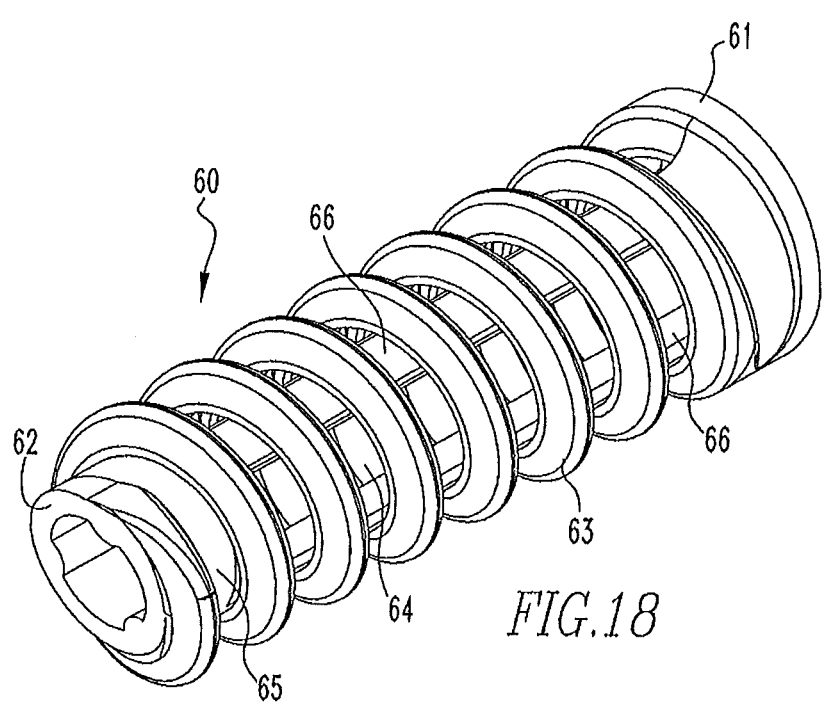
FIG. 18 shows an isometric view of the screw of FIG. 16.
Figure 19:
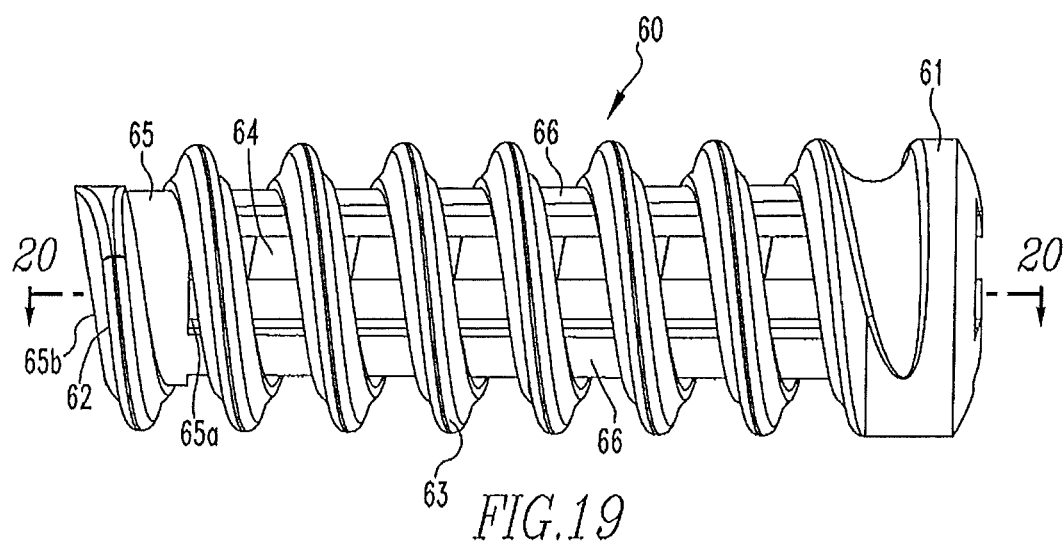
FIG. 19 shows a side view of the screw of FIG. 16.
Figure 20:
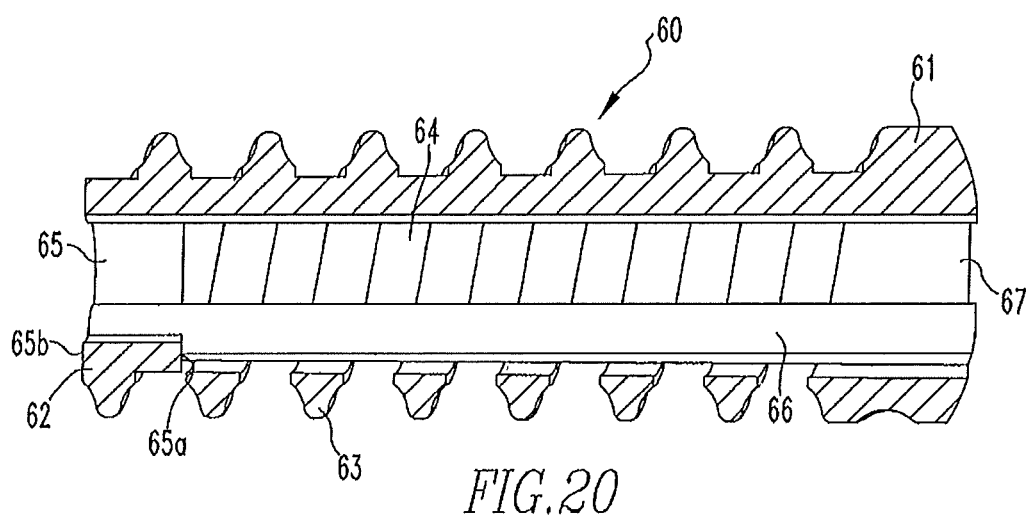
FIG. 20 shows a cross-sectional view of the screw of FIG. 19.

FIGS. 5-7 show the screw 20 for use with the delivery device 10 of the present disclosure. The screw 20 includes a proximal end 21 and a distal end 22. A majority of the screw 20 includes screw threads 23 in the form of an open helical coil, i.e. a connected series of continuous regularly spaced turns extending in a helical or spiral form substantially from the proximal end 21 to the distal end 22 with apertures 24 being defined by the space between the turns of the coil. In other words, interference screw 20 may include an open helical coil defining an internal volume, with the internal volume communicating with the region exterior to the open helical coil through the spacing between the turns of the open helical coil. The distal end 22 also includes a depth stop 25 that extends a partial length of the screw 20. The depth stop 25 includes a proximal end 25*a* and a distal end 25*b*. Additionally, a plurality of longitudinally-extending runners 26 extend along the interior of the screw threads 23.

The distal end 12*b* of the shaft 12 is placed within the interior of the screw 20, via the opening 27, until the proximal end 25*a* of the depth stop 25 engages the depth stop 12*e* of the shaft 12. During insertion of the shaft 12 into the screw 20, the runners 26 engage the grooves 12*d* and become housed within the grooves 12*d*. As shown in FIG. 1, the distal end 12*b* of the shaft 12 also includes hash marks 12*f*, each of which is associated with a number 12*g*. Once the screw 20 is placed on the shaft 12, the proximal end 21 of the screw 20 aligns with one of the hash marks/numbers 12*f*, thereby indicating the length of the screw 20.

FIGS. 8, 9-9A, and 10-15 show an alternative shaft 30 of the present disclosure. The shaft 30 includes an inner member 31 and an outer member 32 disposed over the inner member 31. The proximal end 31*a* of the inner member 31 is similar in shape to the proximal end 12*a* of the shaft 12. The distal end 31*b* of the inner member 31 includes threads 31*c*. Grooves 31*d* extend along the member 31 and intersect the threads 31*c*. Additionally, threads 31*e* are located between the proximal and distal ends 31*a*,31*b* of the member 31. The outer member 32 includes a first section 32*a* and a second section 32*b*. The first section 32*a* has a larger diameter than the second section 32*b*. The first section 32*a* also includes threads 32*c* on an inner wall 32*d* of the outer member 32.

Once the outer member 32 is disposed over the inner member 31, threads 32*c* engage threads 31*e* to move the outer member 32 relative to the inner member 31. Moving the outer member 32 relative to the inner member 31 allows for more or less of the distal end 31*b* of the inner member 31 to be shown. Similar to the distal end 12*b* of the shaft 12, the distal end 31*b* of inner member 31 includes hash marks/numbers (not shown) that align with an end 32*b*' of the second section 32*b*, thereby indicating a length of screw 40 that will be disposed on the distal end 31*b* of the inner member 31. As shown in FIGS. 14 and 15, the outer member 32 is located at different positions along the length of the inner member 31 to allow for screws 40 of different lengths to be loaded on the distal end 31*b* of the inner member 31.

A handle assembly, similar to the handle assembly 11, is coupled to the proximal end 31*a* of the inner member 31. Similar to screw 20, screw 40 includes a proximal end 41 and a distal end 42. The screw 40 includes screw threads 43 in the form of an open helical coil having an interior and a plurality of longitudinally-extending runners 45 extending along the interior of the screw threads 43. Screw 40 is more fully described in United States Patent Application Publication No. 20080154314, the disclosure of which is incorporated herein by reference in its entirety. Once the outer member 32 has been moved to indicate the screw length, the screw 40 is loaded onto the distal end 31*b*, such that a proximal end 41 of the screw 40 engages the end 32*b*' and the runners 45 engage the grooves 31*d* and become housed within the grooves 31*d*.

FIGS. 16-20 show another alternative embodiment of the shaft 50 and screw 60 of the present disclosure. The shaft 50 includes a first portion 51 including a proximal end 51*a* and a distal end 51*b* and a second portion 52 including a first area 52*a* and a second area 52*b*. The proximal end 51*a* is configured to be coupled to a handle assembly, similar to the handle assembly 11. However, other handle assemblies may be used. The first area 52*a* has a smaller diameter than the first portion 51, such that a first depth stop 51*b*' exists at the distal end 51*b* of the first portion 51. The second area 52*b* has a smaller diameter than the first area 52*a* such that a second depth stop 52*c* exists between the first area 52*a* and the second area 52*b*. An end 52*b*' of the second area 52*b* is tapered to allow for easier insertion of the anchor 60 into a bone during ligament reconstruction surgery, as will be further described below. The second portion 52 also includes grooves 53 extending between the first and second areas 52*a*,52*b*. For the purposes of this disclosure, there are three grooves 53. However, the second portion 52 may include a higher or lower number of grooves 53.

Similar to screw 20 shown in FIGS. 5-7, screw 60 includes a proximal end 61 and a distal end 62. A majority of the screw 60 includes screw threads 63 in the form of an open helical coil, i.e. a connected series of continuous regularly spaced turns extending in a helical or spiral form substantially from the proximal end 61 to the distal end 62 with apertures 64 being defined by the space between the turns of the coil. In other words, interference screw 60 may include an open helical coil defining an internal volume, with the internal volume communicating with the region exterior to the open helical coil through the spacing between the turns of the open helical coil. The distal end 62 also includes a depth stop 65 that extends a partial length of the screw 60. The depth stop 65 includes a proximal end 65*a* and a distal end 65*b*. Unlike the open depth stop 25 of screw 20 most clearly shown in FIG. 5, the depth stop 65 of screw 60 is a closed depth stop, most clearly shown in FIG. 18. Additionally, a plurality of longitudinally-extending runners 66 extend along the interior of the screw threads 63.

The second portion 52 of the shaft 50 is placed within the interior of the screw 60, via the opening 67, until the proximal end 65*a* of the depth stop 65 engages the second depth stop 52*c* of the shaft 50. During insertion of the shaft 50 into the screw 60, the runners 66 engage the grooves 53 and become housed within the grooves 53. The screws 60 may be of a variety of lengths. For example, a screw 60 may be of such length that its proximal end 61 would engage the first depth stop 51*b*'.

As described above, during ligament reconstruction surgery, the end of the graft ligament is placed in the bone tunnel and then the interference screw 20,40,60 is advanced into the bone tunnel via the use of shafts 12,30,50 so that the interference screw 20,40,60 extends parallel to the bone tunnel and simultaneously engages both the graft ligament and the side wall of the bone tunnel. The screws 20,40,60 may be used in either the femoral or tibial tunnels. Methods of ligament reconstruction via use of the screws 20,40,60 is further shown in the '314 publication shown above.

Figure 21:
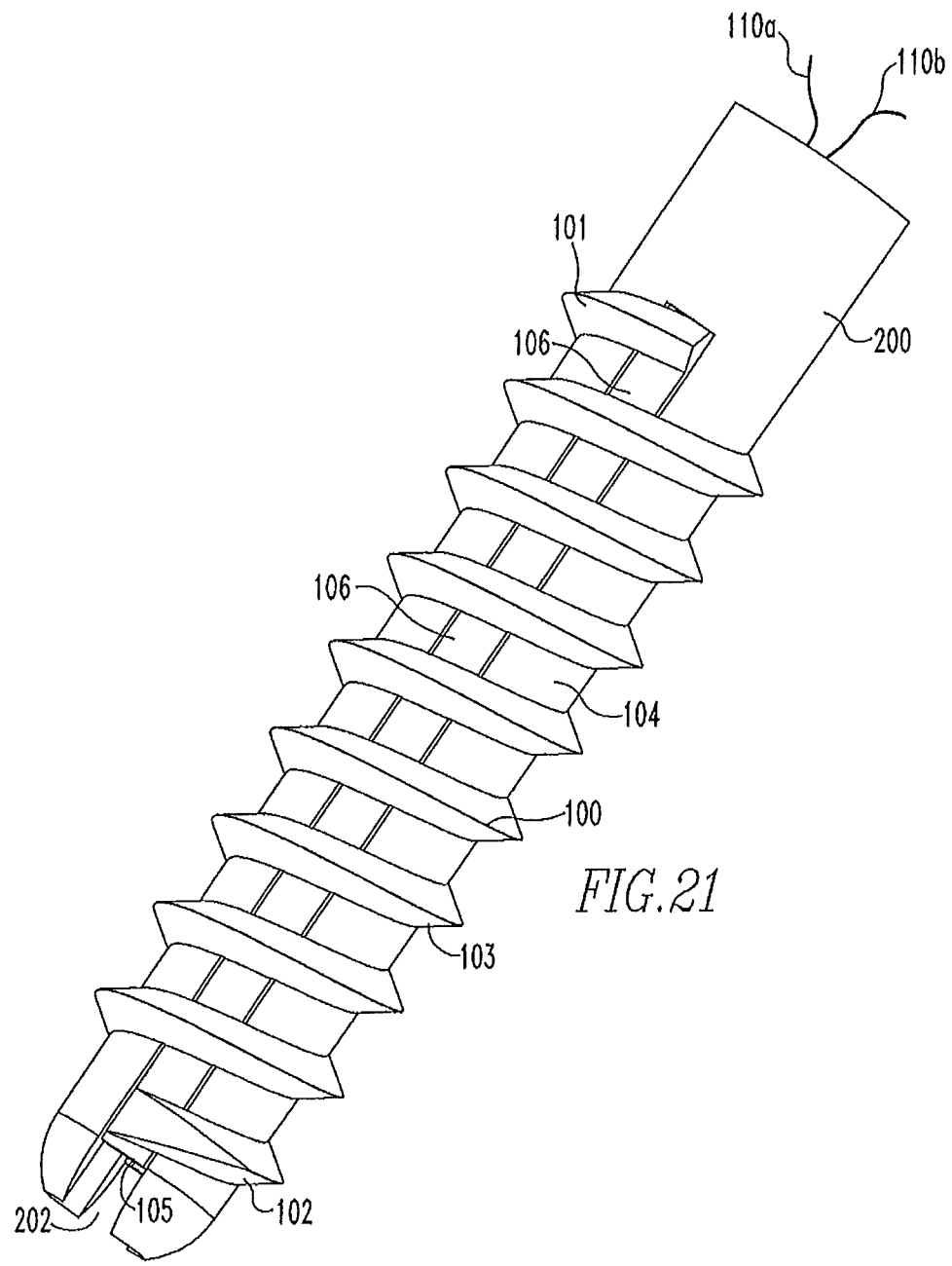
FIG. 21 shows an isometric view of a fourth embodiment of a shaft of the present disclosure and a screw for use with the shaft.
Figure 22:
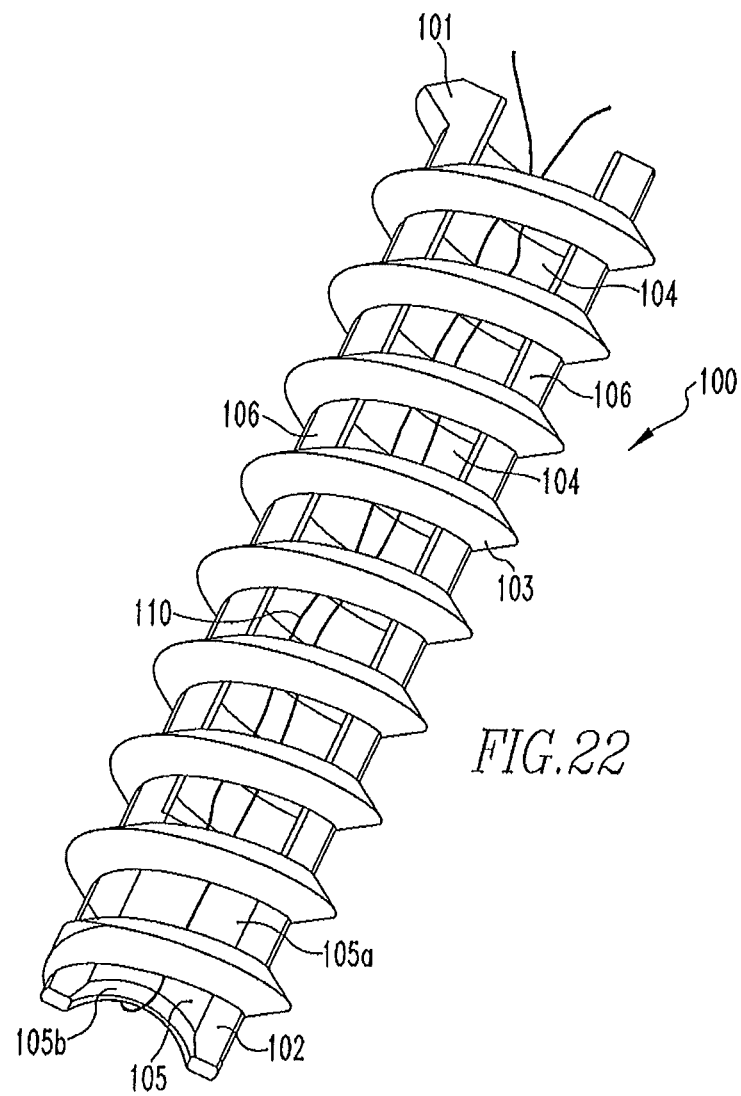
FIG. 22 shows an isometric view of the screw of FIG. 21.

FIGS. 21-23 show yet another alternative embodiment of the screw 100 and the delivery device 200 of the present disclosure. The screw 100 includes a proximal end 101 and a distal end 102. A majority of the screw 100 includes screw threads 103 in the form of an open helical coil, i.e. a connected series of continuous regularly spaced turns extending in a helical or spiral form substantially from the proximal end 101 to the distal end 102 with apertures 104 being defined by the space between the turns of the coil. In other words, interference screw 100 may include an open helical coil defining an internal volume, with the internal volume communicating with the region exterior to the open helical coil through the spacing between the turns of the open helical coil. The distal end 102 also includes a suture bridge 105 that extends a partial length of the screw 100. The suture bridge 105 includes a proximal end 105a and a distal end 105b. The distal end 105b includes a concave shape. A flexible member 110, such as a suture, is housed within the screw 100, such that the suture 110 extends around the distal end 105b of the bridge 105. Additionally, longitudinally-extending runners 106 extend from the suture bridge 105 and along the interior of the screw threads 103. For the purposes of this disclosure, there are two longitudinally extending runners 106. However, more or less than two runners are within the scope of this disclosure.

The delivery device 200 includes a distal end 201 having a slot 202 and grooves 203 extending from the slot 202 on each side of the device 200. As shown in FIG. 21, the screw 100 is located on the distal end 201 such that the suture bridge 105 is housed within the slot 202 and the runners 106 are housed within the grooves 203. The delivery device 200 is cannulated, such that when the screw 100 is located on the device 200, the suture ends 110a,110b extend through the cannulation 204.

FIGS. 24-26 show a screw 300 similar to screw 100. However, screw 300 additionally includes a pointed tip 311 located on the distal end 302. The tip 311 includes a through hole 312. The hole 312 helps in locating the suture 110 within the interior of the screw 300. As shown in FIG. 24, the screw 300 is located on the distal end 201 of delivery device 200 such that the suture bridge 305 is housed within the slot 202 and the runners 306 are housed within the grooves 203. As stated above, the delivery device 200 is cannulated, such that when the screw 300 is located on the device 200, the suture ends 110a,110b extend through the cannulation 204, as shown in FIG. 24.

For clarity purposes, only the distal end 201 of the device 200 is shown. However, the device 200 would include a proximal end, similar to the devices above, which may be coupled to a handle assembly, similar to handle assembly 11 above. The screws 100,300 are used in the repair of soft tissue, specifically to re-attach tissue to bone. One example of this repair is when the screw 100,300 is delivered into bone via the use of device 200, the device 200 is removed from screw 100,300, the tissue is placed on the bone to be adjacent the screw 100,300, the suture ends 110a,110b are pulled through the tissue, and then the suture ends 110a,110b are tied. A hole may be made in the bone prior to insertion of the screw 100,300 into the bone. However, screw 300 may be inserted into bone without first making a hole in the bone. In this case, the pointed tip 311 is used to start insertion of the screw 300 into the bone and then rotary motion may be used to complete insertion of the screw 300 into the bone. Other methods of tissue repair via use of these screws and delivery device may also be used.

The handle 11a of handle assembly 11 is made from plastic, however, other non-metal and metal materials may also be used. The shape and size of handle 11a may be any shape and size necessary to help facilitate insertion of the screw 20 into bone. The coupler 11b is made from a metal material, such as stainless steel or titanium, but may be made from other metal and non-metal materials that are strong enough to withstand the forces applied during surgery. The coupler 11b is press-fit to the handle 11a, but may be coupled to the handle 11a in any other manner known to those of skill in the art. The size and shape of the coupler 11b may be any size and shape necessary to help facilitate insertion of the screw 20 into bone. The channel 11b' may be any length necessary and the opening 11b" may be any shape necessary to facilitate coupling of the shaft 12 to the coupler 11b.

The shaft 12 is made from a metal material, such as stainless steel and titanium, however, other metal and non-metal materials that would withstand the forces applied during surgery may be used. The diameter of the shaft 12 may vary. The proximal end 12a of the shaft 12 may be any shape necessary to facilitate insertion of the end 12a through opening 11b" and into channel 11b'. The number of threads 12c and grooves 12d may vary and the lengths of the grooves 12d may also vary. The location of depth stop 12e may also vary based on the diameter of the shaft 12 and the diameter of the screw 20 that is used. The grooves 12d, depth stop 12e, and threads 12c may be formed by any method known to one of skill in the art.

The screw 20 is made from a polymer material via a molding method. However, other material, which would allow the screw 20 to withstand forces applied during surgery, and other methods of making may be used. The depth stop 25 is open ended and doesn't extend the entire inner diameter of the screw 20. The amount of screw inner diameter that the depth stop 25 covers may vary and the length of the depth stop 25 may vary based on the diameter of the screw. The number and length of the runners 26 may also vary. Once the screw 20 is located on the shaft 12, the distal end 12b of the shaft 12 extends from the distal end 22 of the screw 20. During insertion of the screw 20 into bone, the threads 12c create threads in the bone, thereby creating a seat for the screw threads 23, as described more fully in the '314 publication. The amount of the distal end 12b of the shaft 12 that extends from the distal end 22 of the screw 20 may vary.

The diameters of the first and second sections 32a,32b of outer member 32 may vary and the number of threads 32c may also vary. The number of threads 31c,31e and grooves 31d may vary and the lengths of the grooves 31d may also vary. The inner and outer members 31,32 are made from a metal material, such as stainless steel and titanium, and via a method known to one of skill in the art. However, other materials may also be used. The screw 40 is made from a polymer material via a molding method. However, other material and methods of making may be used. The number and length of the runners 45 may also vary. Once the screw 40 is located on the shaft 30, the distal end 31b of the shaft 30 extends from the distal end 42 of the screw 40. During insertion of the screw 40 into bone, the threads 31c create threads in the bone, thereby creating a seat for the screw threads 43, as described more fully in the '314 publication. The amount of the distal end 31b of the shaft 30 extending from the screw 40 may vary.

The shaft 50 is made from a metal material, such as stainless steel or titanium, but may be made from another metal material or a non-metal material that is strong enough to withstand the force applied to the shaft 50 during surgery.

The shaft 50 may be made via a method known to one of skill in the art. The diameters of the first and second portions 51,52 may vary along with the number and lengths of the grooves 53 and the locations of the depth stops 52c,51b' may vary based on the diameter of the screw 60 or other factors. Rather than being tapered, the end 52b' may be designed in another manner to allow easier insertion of the screw 60 into bone. The screw 60 is made from a polymer material via a molding method. However, other material, which would allow the screw to withstand the forces applied during surgery, and other methods of making may be used. The number and length of the runners 66 may also vary. Once the screw 60 is located on the shaft 50, the second portion 52 of the shaft 50 extends from the distal end 62 of the screw 60. The amount of the second portion 52 extending from the screw 60 may vary. Additionally, the length of the depth stop 65 may also vary based on the diameter of the screw 60 or other factors.

The delivery device 200 is made from a metal material, such as stainless steel or titanium, but may be made from a non-metal material that is strong enough to withstand the forces applied to the device 200 during surgery. The delivery device 200 is made via a method known to one of skill in the art. The screws 100,300 are made from a polymer material and via a molding process, however, other material, which would allow the screw to withstand the forces applied during surgery, and other processes known to one of skill in the art may be used. The suture bridge 105 may have a distal end 105b having a shape other than concave and the length of the suture bridge 105, the slot 202, and the grooves 203 may vary. The size and the shape of the hole 312 may vary.

For example, FIGS. 27-33 show yet another alternative embodiment of a screw (anchor) 400 and the delivery device 200 of the present disclosure. The screw 400 includes a proximal end 401 and a distal end 402.

The distal end 402 also includes a suture bridge 405 that extends a partial length of the screw 400. The suture bridge 405 includes a proximal end 405a and a distal end 405b.

The distal end 405b of the suture bridge 405 has a thickness greater than a thickness of the proximal end 405a of the suture bridge 405. In one example, the distal end 405b includes a convex shape. A convenient example of the screw 400 has a suture bridge with a bulbous profile. A flexible member 410, such as a suture, is housed within the screw 400, such that the suture 110 extends around the distal end 405b of the bridge 405.

A majority of the screw 400 includes screw threads 403 in the form of an open helical coil, i.e. a connected series of continuous regularly spaced turns extending in a helical or spiral form substantially from the proximal end 405a of the suture bridge 405 to the proximal end 401 of the screw 400 with apertures 404 being defined by the space between the turns of the coil. In other words, the screw 400 may include an open helical coil defining an internal volume, with the internal volume communicating with the region exterior to the open helical coil through the spacing between the turns of the open helical coil.

Figure 30:
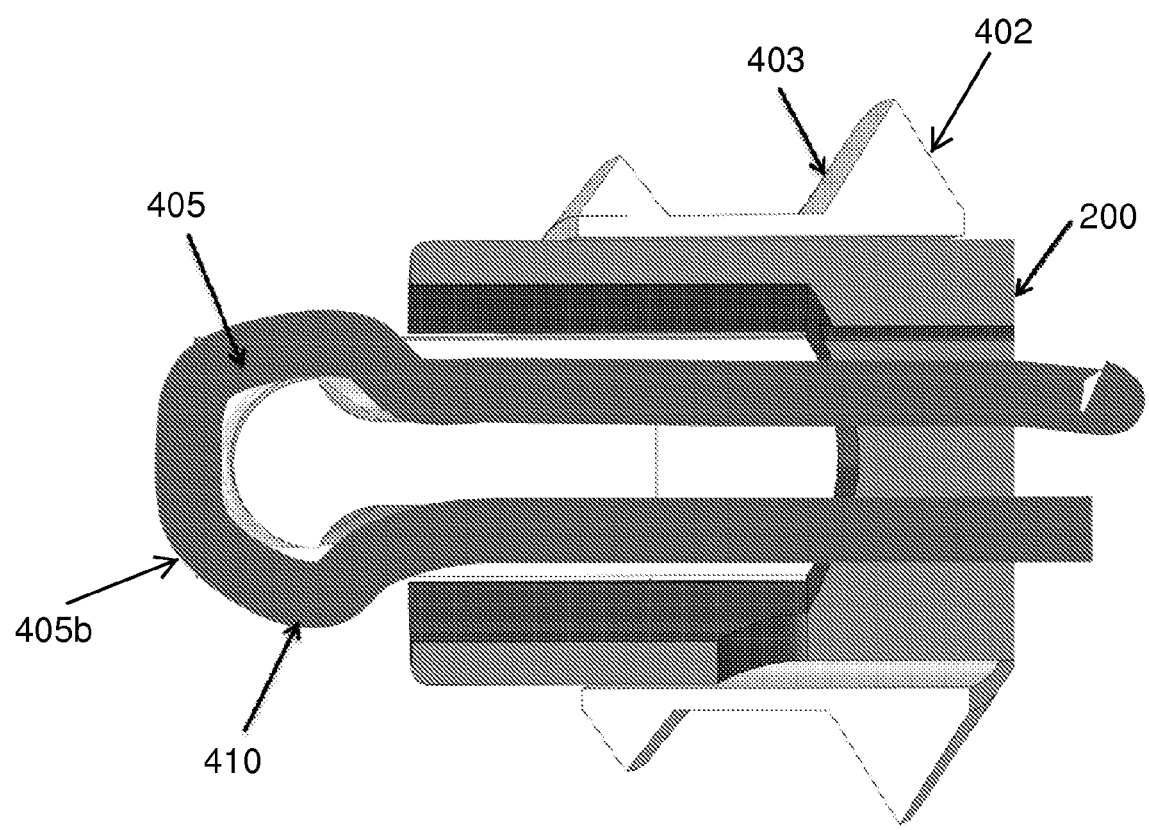
FIG. 30 shows a close up view of the distal end of the anchor of FIG. 29.

In one example of the screw 400, the screw threads 403 cover the proximal end 405a of the suture bridge 405 (best seen in FIG. 30). In another example of the screw 400, the screw threads 403 start at proximal end 105a of the suture bridge 105. In some examples, the screw threads 403 may define, at least in part, an anchor body and may be referred to as such.

Longitudinally-extending runners (ribs) 406 extend from the suture bridge 405 and along the interior of the screw threads 403. For the purposes of this disclosure, there are two longitudinally extending runners 406. However, more or less than two runners are within the scope of this disclosure.

Figure 27:
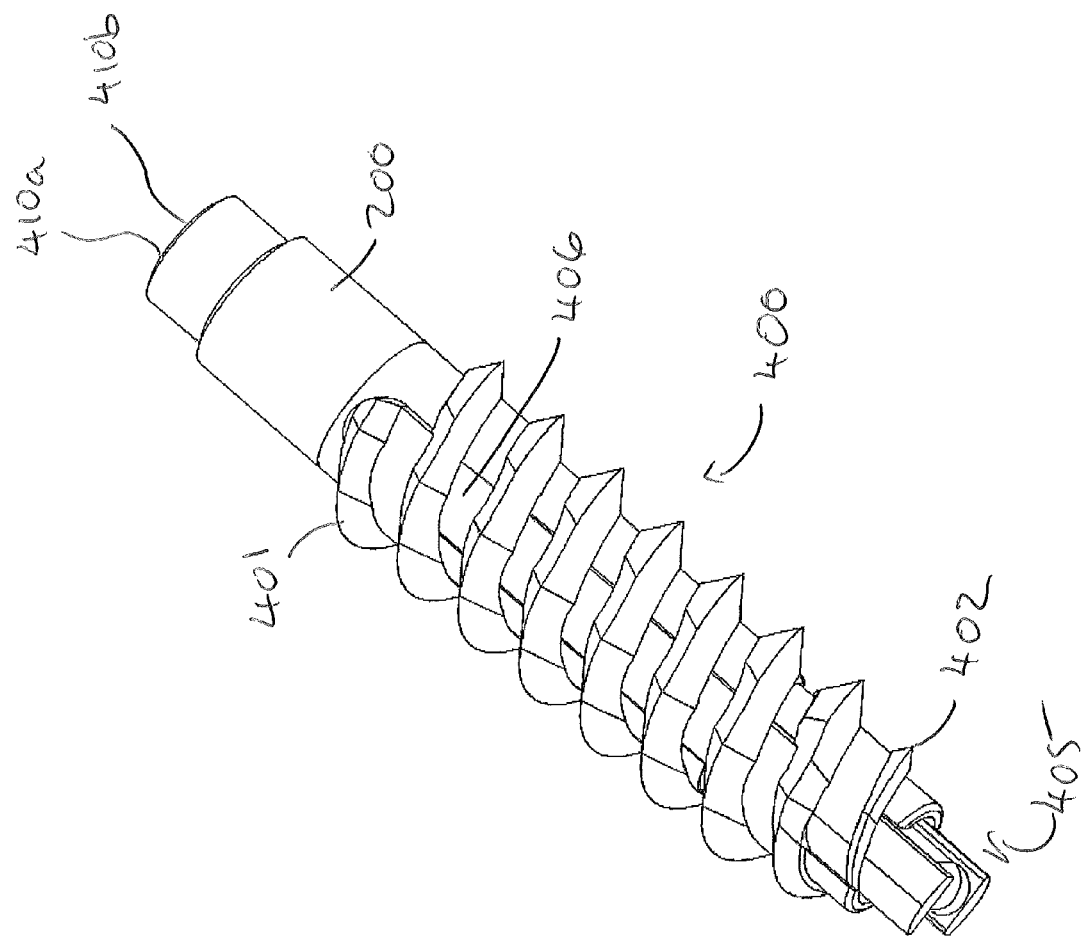
FIG. 27 shows an isometric view of an example anchor with suture bridge and example inserter shaft for the anchor.

The delivery device 200 includes a distal end 201 having a slot 202 and grooves 203 extending from the slot 202 on each side of the device 200. As shown in FIG. 27, the screw 400 is located on the distal end 201 such that the proximal end 405a of the suture bridge 405 is housed within the slot 202 and the runners 406 are housed within the grooves 203. The delivery device 200 is cannulated such that when the screw 400 is located on the device 200, the suture ends 410a, 410b extend through the cannulation 204.

The general suture bridge design described above with reference to FIGS. 27-33 may be advantageous to screws (anchors) made from bioabsorbable material. Compared to other materials, such as polyetheretherketone (PEEK), a bioabsorbable material is weaker and more brittle. Testing shows that other suture bridge designs, while adequate for devices made from PEEK, do not provide sufficient bridge strength for products made from bioabsorbable material.

FIGS. 28-31 show a convenient example of the suture bridge 405 suitable for an open-architecture anchors (e.g., fenestrated anchor) fabricated from bioabsorbable material.

Figure 28:
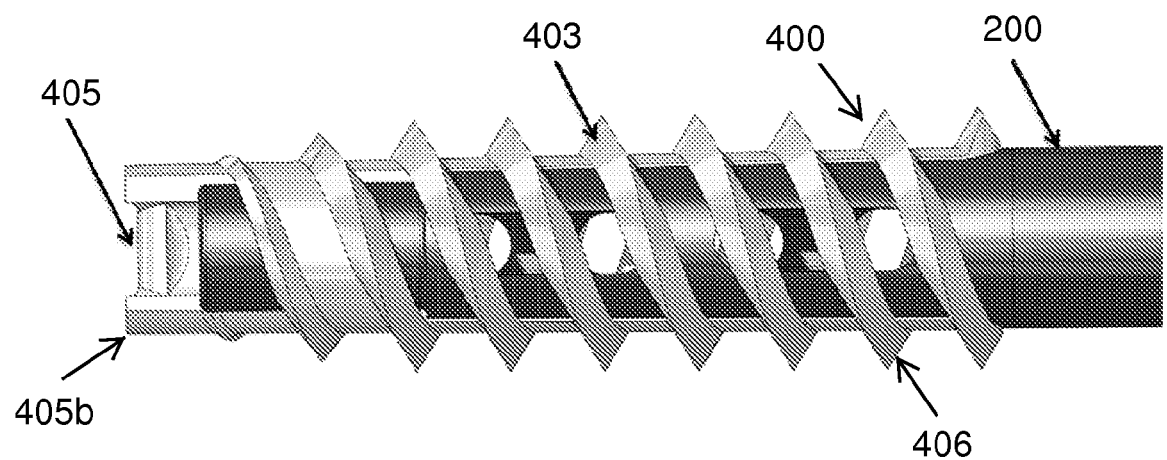
FIG. 28 shows a side view of the shaft and anchor of FIG. 27.

FIG. 28 shows a working example of a device 400 in which a bulbous distal end 405b of the suture bridge 405 is outside an inserter 200. The foregoing arrangement allows additional space/volume for the suture bridge 405 to occupy and for the device 400 to still accommodate a full suture load.

Figure 29:
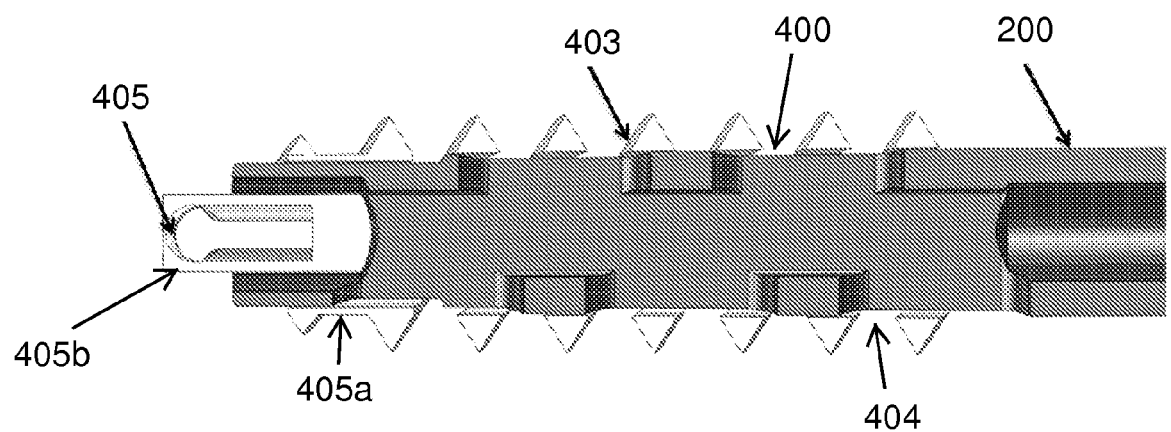
FIG. 29 shows a cross-sectional view of FIG. 28.

FIG. 29 shows a cross section view of working end of the device 400—the same section of the device depicted in FIG. 28. In this case, the cross section is rotated 90 degrees. The bulbous distal portion 405b of the suture bridge 405 protrudes outside the inserter 200 and is enlarged to better distribute the load imparted onto the suture bridge 405 by a suture.

FIG. 30 shows a close up view of the distal end 402 of the device 400. The bulbous portion 405b of the suture anchor 405 is outside the envelope of the inserter 200. The extension of the bulbous portion 405b of the bridge outside 405 of the inserter 200 allows there to be room for a suture 410 to occupy.

Figure 31:
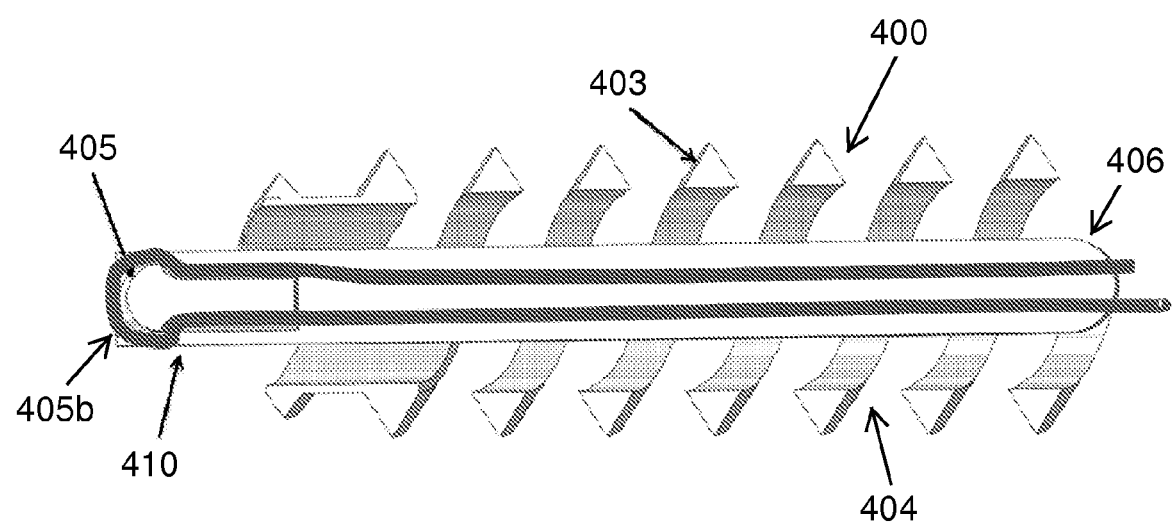
FIG. 31 shows a cross-sectional view of the anchor of FIG. 27.
Figure 32:
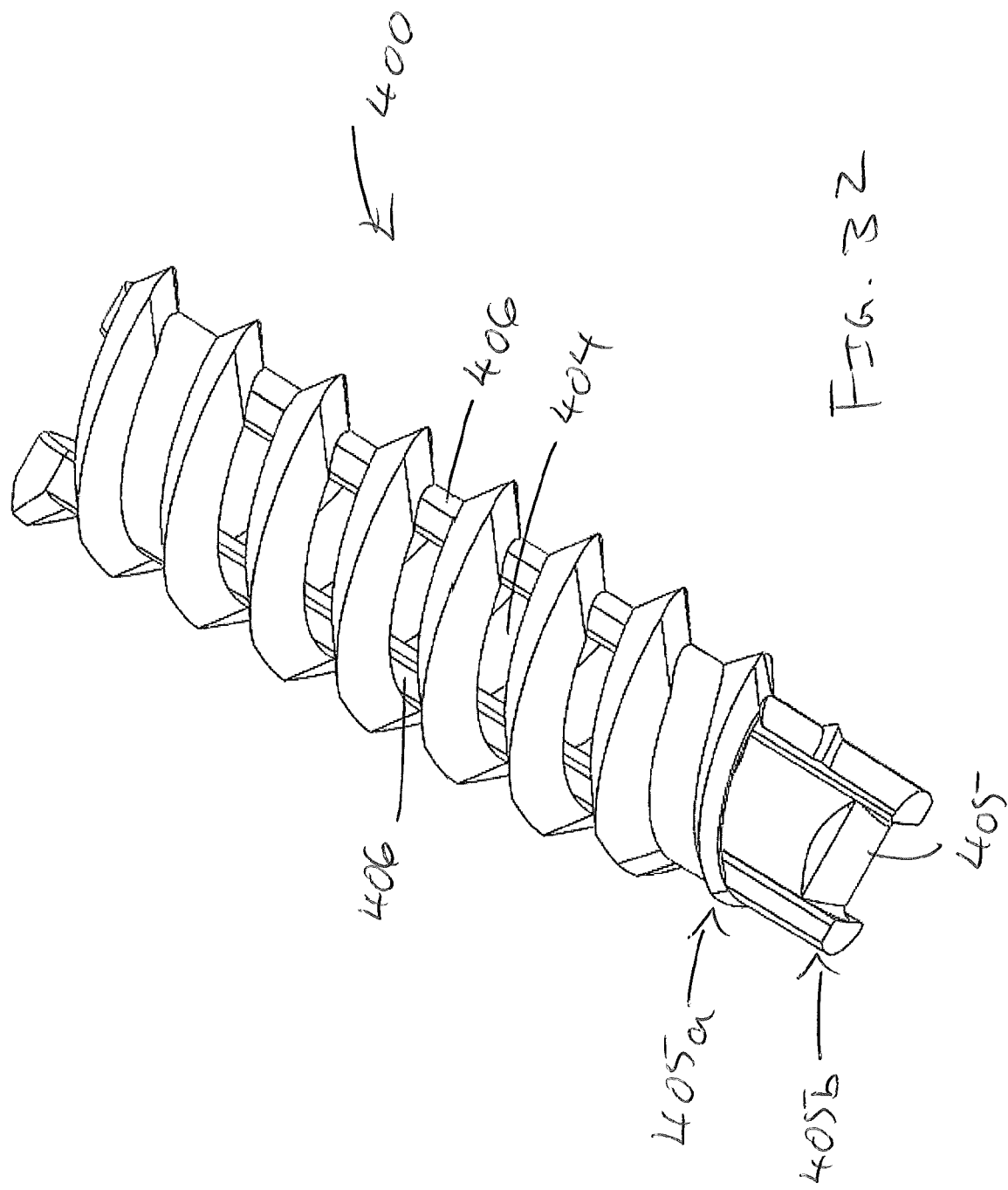
FIG. 32 shows an isometric view of the anchor of FIG. 27.
Figure 33:
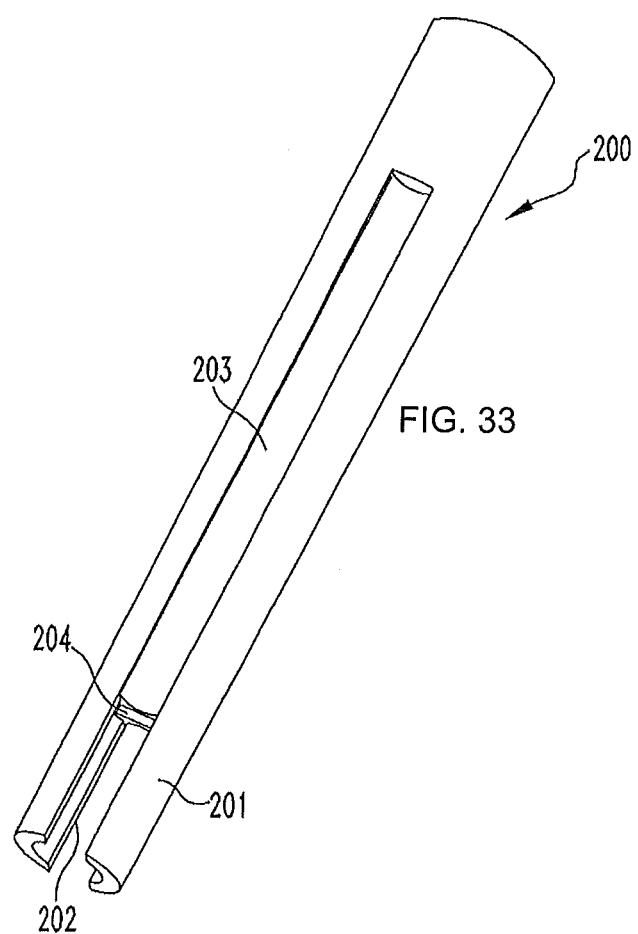
FIG. 33 shows an isometric view of the shaft of FIG. 27.

FIG. 31 shows a cross section view of the device 400 removed from the inserter 200. The bulbous portion 405b of the suture anchor 405 can be seen, as can the interaction between the suture 410, suture bridge 405 and the anchor body 403.

While the suture bridge 405 and its examples are described above in the context of a single suture, the foregoing disclosure also applies to a device loaded with multiple sutures (e.g., three) and the associated suture load. Because the distal (thick) end of the suture bridge 405 extends beyond the inserter 200, the suture bridge 405 is able to accommodate a large suture load. Because the distal end 402 of the bridge 405 is bulbous, the suture bridge 405 can withstand significant loads applied by multiple sutures.

The general suture bridge design contemplates other variations providing a suture bridge that is structurally strong to hold up to loads imparted onto it by a suture(s), particularly during knot tying by a surgeon. In one example, the bulbous portion of the suture bridge extends distally further increasing the load carrying capability of the suture bridge. In other example, the diameter of the suture bridge extends beyond the width of the longitudinal ribs/runners further enhancing the strength of the suture bridge.

Figure 34:
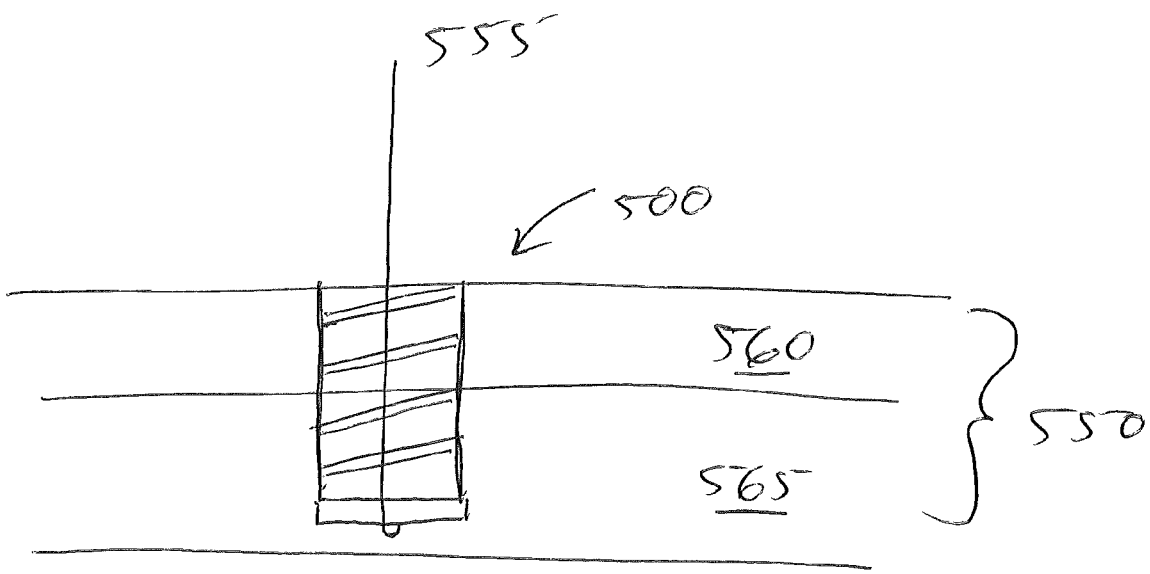
FIG. 34 shows a cross-sectional view of an anchor inserted into bone.

FIG. 34 shows an anchor 500 inserted into bone 550. The anchor 500 holds one or more sutures 555 used, for example, to tie soft tissue (not shown) down to the bone 550. The bone 550 has a hard outer layer of cortical bone 560 and soft inner layer of cancellous bone 565. There may be more layers of bone. The number of layers, however, is not important to the following disclosure but rather there is one layer harder than the other. The hard outer layer of cortical bone or simply "cortical layer" 560 imparts a strong reactionary force on the anchor 500. It is observed that this reactionary force is a cause of failure in anchors, particularly in anchors having an open-architecture design and made from bioabsorbable material, such as the examples described above with reference FIGS. 27-33.

In testing, open-architecture anchors made from bioabsorbable material inserted into 25/5 pcf bilayer bone block simulating average humeral head bone, exhibit a novel failure mode of thread stripping from the anchors. Failure of the threads initiates in the simulated cortical layer (25 pcf) and cascades down the anchors as each subsequent thread encounters the simulated cortical layer during a pullout event, such as when a surgeon tensions a suture to tie a knot. Failure initiates in the distal most threads of the anchors because a disproportionately high amount of the (axial) load applied by the suture to the anchors is reacted by the distal most threads, which are embedded in the denser (harder) cortical layer. The failure of the distal most threads and the subsequent cascade of thread failure lead to reduced fixation strength of the anchors in average humeral head bone quality as represented by 25/5 pcf bone block.

Figure 35:
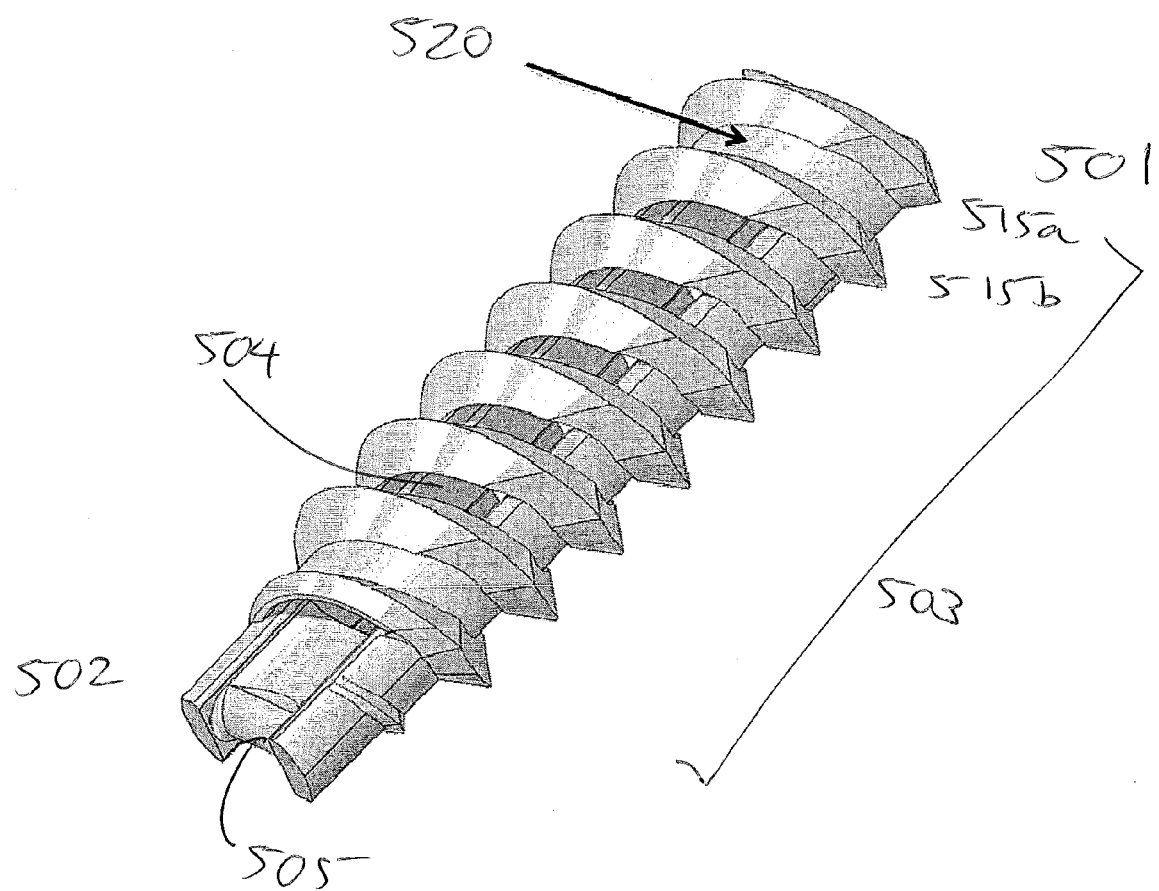
FIG. 35 shows an isometric view of an example anchor with suture bridge and proximal reinforcement.

FIG. 35 shows an example of the anchor 500 designed to handle the reactionary force imparted by the cortical layer 560 and to prevent a pullout failure. The anchor 500 includes a proximal end 501 and a distal end 502. The distal end 502 includes a suture bridge 505 that extends a partial length of the anchor 500, such as the suture bridge 405 described above with reference to FIGS. 28-31.

A majority of the anchor 500 includes screw threads 503 in the form of an open helical coil, i.e. a connected series of continuous regularly spaced turns extending in a helical or spiral form substantially from the proximal end 505a of the suture bridge 505 to the proximal end 501 of the anchor 500. The terms screw threads and helical coil are used interchangeably herein. The anchor 500 includes apertures 504 being defined by the space between turns of the helical coil 503. The anchor 500 is further characterized by a number of turns per a given length, called "screw thread pitch" or simply "pitch."

At the proximal end 501 of the anchor 500, webbing 520 extends between adjacent turns 515a and 515b of the coil 503. The number of turns with webbing in between is a function of the thickness of the cortical layer 560 and the pitch of the helical coil 503. Because the anchor 500 (and its example) is reinforced, proximally, according to the foregoing relationship, the inserted anchor 500 supports a greater axial load than compared to non-reinforced anchors. The inserted anchor 500 (and its example) exhibits a greater resistance to being pulled out of bone or "pull out strength" than compared to anchors without proximal reinforcement, particularly, in the hard layer and soft layer makeup found in typical humeral head bone stock.

In one example of the anchor 500, the number of turns with webbing in between increases as the thickness of the cortical layer 560 and/or the pitch of helical coil 503 increases.

As shown in FIG. 35, an example of the anchor 500 includes a proximal web between the distal most thread 515a and the second most distal thread 515b. This example of the anchor 500 has a dual lead thread meaning there are two "ridges" wrapped around the cylinder of the body of the anchor 500. With a dual lead thread arrangement, the web 520 circumnavigates the proximal end 501 as shown. Because of the screw thread pitch of the anchor 500, the proximal web 520 extends through the full cortical layer thickness of the humeral head bone stock providing reinforcement of the anchor through the entire cortical layer.

The example of the anchor 500 shown in FIG. 35 has one "distal" gap between the distal most thread 515a and the second most distal thread 515b filled with webbing 520. Other examples of the anchor 500 may have more than one distal gap between threads filled with webbing 520. The extent the webbing 520 progresses distally down the anchor 500 is based on the thicknesses of the cortical layer into which the anchor 500 is to be inserted and the pitch of the anchor 500.

Some examples of the anchor 500 have different numbers of turns corresponding to different cortical layer thicknesses. The thickness of the cortical layer varies from bone to bone, e.g., the cortical layer of the humeral head is thinner than the cortical layer of the tibia. Proximal reinforcement of the anchor 500 may be advantageously tailored to a specific application e.g., the proximal reinforcement of an anchor used in shoulder repair is different than the proximal reinforcement of an anchor used in knee repair.

FIG. 36 shows an example anchor 600 having a proximal end 601 and distal end 602. The anchor 600 includes, at the distal end 602, a suture bridge 605 (such as one described above with reference to FIGS. 27-31). The anchor 600 further includes two open helical coils 603a, 603b in a dual lead thread arrangement. The two open helical coils 603a, 603b extend from the suture bridge 605 toward the proximal end 601. Webbing 620 extends between adjacent turns of one of the two helical coils. The configuration of the anchor 600 strengthens/reinforces a substantial length of the anchor 600, including the entire length. At the same time, the configuration of the anchor 600 provides a degree of openness promoting desirable bony ingrowth. It may be convenient in some examples of the anchor 600 to characterize the webbing 620 as being continuous (i.e., continuous webbing).

FIGS. 37 and 38 show an example anchor 700 having a proximal end 701 and distal end 702. The anchor 700 includes, at the distal end 702, a suture bridge 705 (such as one described above with reference to FIGS. 27-31). A majority of the anchor 700 includes a plurality of regularly spaced turns 703 extending in a helical or spiral form from a proximal end 705a of the suture bridge 705, approximately, to the proximal end 701 of the anchor 700. Webbing 720 extends between each turn of the plurality of regularly spaced turns 703 and an adjacent turn (e.g., turns 703a and 703b). The webbing 720 gives the anchor 700 torsion and compression strength. The webbing 720 defines apertures 722, which may be rectangular (square) or oval (circle) in shape. The apertures 722 give the anchor 700 a degree of openness promoting desirable bony ingrowth. It may be convenient in some examples of the anchor 700 to characterize the webbing 720 as being interrupted or perforated (i.e., interrupted/perforated webbing).

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An anchor comprising:
   a suture bridge having a proximal end and distal end, the distal end of the suture bridge having a thickness greater than a thickness of the proximal end of the suture bridge and defining the distal terminus of the anchor;
   at least two ribs extending from the proximal end of the suture bridge to a proximal end of the anchor; and
   at least one open helical coil wrapping around the at least two ribs and extending, substantially, from the proximal end of the suture bridge to the proximal end of the anchor, the at least one open helical coil defining an internal volume communicating with a region exterior to the anchor through apertures between turns of the at least one open helical coil;
   wherein the at least one open helical coil and the proximal end of the suture bridge define a space extending to a region adjacent the distal end of the suture bridge, the space configured for receipt of a distal end of a delivery device, such that the distal end of the suture bridge projects beyond the distal end of the delivery device.

2. The anchor of claim 1 wherein the suture bridge has a bulbous profile.

3. The anchor of claim 1 wherein the distal end of the suture bridge is convex in shape.

4. The anchor of claim 1 wherein the at least one open helical coil covers the proximal end of the suture bridge.

5. The anchor of claim 1 wherein the anchor is made from a bioasborable material.

6. The anchor of claim 1 further comprising, at the proximal end of the anchor, webbing extending between adjacent turns of the at least one helical coil, a number of turns with webbing in between configured to be a function of the thickness of the cortical layer of bone and the pitch of the at least one helical coil.

7. The anchor of claim 6 wherein the number of turns with webbing in between is configured to increase with an increase in the thickness of the cortical layer of bone, increase in the pitch of the at least one helical coil, or an increase in both.

8. The anchor of claim 6 wherein the anchor includes two open helical coils in a dual lead thread arrangement, and wherein the webbing extends between adjacent turns of one of the two helical coils.

9. The anchor of claim 6 wherein the at least one open helical coil includes a plurality of regularly spaced turns; and wherein the webbing extends between each pair of turns and defines openings through which the internal volume of the anchor communicates with the region exterior to the anchor.

10. The anchor of claim 1, further comprising at least one suture routed over the distal end of the suture bridge, such that the at least one suture projects beyond the distal end of the delivery device.

11. The anchor of claim 1, wherein a diameter of the suture bridge extends beyond a width of the at least two ribs.

* * * * *